United States Patent [19]

Anderson et al.

[11] Patent Number: 4,882,282
[45] Date of Patent: Nov. 21, 1989

[54] DNA SEQUENCES ENCODING BOVINE INTERLEUKIN-2

[75] Inventors: Dirk M. Anderson, Seattle; Paul E. Baker, Bainbridge Island; Michael A. Cantrell, Seattle; Douglas P. Cerretti, Seattle; David J. Cosman, Seattle; Steven D. Gimpel, Seattle; Kenneth H. Grabstein, Seattle; Alf D. Larsen, Seattle; Kate N. McKereghan, Seattle, all of Wash.

[73] Assignee: Immunex Corporation, Seattle, Wash.

[21] Appl. No.: 888,994

[22] Filed: Jul. 31, 1986

Related U.S. Application Data

[63] Continuation-in-part of Ser. No. 766,643, Aug. 16, 1985, abandoned.

[51] Int. Cl.[4] ............... C12N 1/00; C12N 15/00; C12P 2/00; C12P 17/34
[52] U.S. Cl. ................... 435/252.3; 435/68; 435/70; 435/91; 435/255; 435/172.3; 435/320; 536/27; 930/11; 930/29; 930/37; 930/38; 930/56; 930/60; 930/69
[58] Field of Search ............ 435/68, 70, 172.3, 317.1, 435/320, 243; 536/22; 935/11, 28, 29, 3 F, 38, 56, 60, 69, 72

[56] References Cited

U.S. PATENT DOCUMENTS 4,738,327 4/1988 Taniguchi et al. ............... 455/243

FOREIGN PATENT DOCUMENTS 0073635 3/1983 European Pat. Off. .
0088622 9/1983 European Pat. Off. .

OTHER PUBLICATIONS

Miller-Edge et al. (1984) Vetinary Immunology and Immunopathology 4: 119–30.
Morgan and Ruscetti, "Selective In Vitro Growth of T Lymphocytes from Normal Human Bone Marrows," *Science* 193:1007 (1976).
Ruscetti, et al., "Functional and Morphologic Characterization of Human T Cells Continuously Grown In Vitro," *J. Immunol.* 119:131 (1977).
Gillis & Smith, "Long Term Culture of Tumor-Specific Cytotoxic T Cells," *Nature* 268:154 (1977).
Farrar, et al., "Biochemical Relationship of Thymocyte Mitogenic Factor and Factors Enhancing Humoral and Cell-Mediated Immune Responses," *J. Immunol.* 121:1353 (1978).
Gillis, et al., "T Cell Growth Factor: Parameters of Production and a Quantitative Microassay for Activity," *J. Immunol.* 120:2027 (1978).

(List continued on next page.)

*Primary Examiner*—Thomas G. Wiseman
*Assistant Examiner*—S. Seidman
*Attorney, Agent, or Firm*—Jerald Nagae; Scott G. Hallquist; Christopher L. Wight

[57] ABSTRACT

A chemically-synthesized oligonucleotide composing a portion of the nucleotide sequence of the human IL-2 is employed as a probe to isolate the gene coding for human IL-2. The human IL-2 gene is selected from a cDNA library prepared from RNA produced by mitogen-stimulated Jurkat cells. Double-stranded cDNA is prepared from polyadenylated RNA extracted from bovine cells thought to produce interleukin-2. Such cDNA is inserted within a plasmid vector and the recombinant plasmid employed to transform hosts. Plasmid DNA, prepared from pools of the transformed hosts, is hybridized with a probe composed of a large portion of the coding sequence of the human IL-2 gene. Pools of host cells that provide signal to the human cDNA probe are identified, subdivided, and rescreened until a single positive colony is identified. Bovine plasmid cDNA is prepared from this colony, and the bIL-2 gene is sequenced. The plasmid DNA is employed to express recombinant bovine IL-2 in yeast and bacterial expression systems, with the expressed bovine IL-2 purified to homogeneity by one or more reverse phase high-performance liquid chromatography procedures.

6 Claims, 4 Drawing Sheets

OTHER PUBLICATIONS

Gillis, et al., "Biochemical Characterization of Lymphocyte Regulatory Molecules," *J. Immunol.* 124:1954 (1980).

Gillis, et al., "Biochemical and Biologic Characterization of Lumphocyte Regulatory Molecules," *J. Exp. Med.* 150:849 (1979).

Watson, et al., "Biochemical and Biological Characterization of Lumphocyte Regulatory Molecules," *J. Exp. Med. 150:1510 (1979).*

Watson, "Continuous Proliferation of Murine Antigen-Specific Helper T Lumphocytes in Culture," *J. Exp. Med.* 150:1510 (1979).

Baker and Knoblock, "Bovine Costimulator. I. Production Kinetics, Partial Purification, and Quantification in Serum-Free Iscove's Medium," II. Generation and Maintenance of a Bovine Costimulator-Dependent Bovine Lymphoblastoid Cell Line, *Vet. Immuno. Immuhopath.* 3:365 (1982), and *Vet. Immunol. Immunopath.* 3:381 (1982).

Splitter and Miller-Edge, "Interleukin 2 (IL-2) Assays Compared By Measuring Bovine IL-2," *Fed. Proc.* 42:447 (1983).

Ceretti, et al., "Cloning, Sequence, and Expression of Bovine Interleukin 2" *Proc. Natl. Acad. Sci.* 83:3223 (1986).

Reeves, et al., "Molecular Cloning of a Functional Bovine Interleukin 2 cDNA," *Proc. Natl. Acad. Sci.* 83:3228 (1986).

```
             1                                         10                                          20          *
           Met Tyr Arg Met Gln Leu Leu Ser Cys Ile Ala Leu Ser Leu Val Thr Asn Ser Ala Pro
TGCCACA ATG TAC AGG ATG CAA CTC CTG TCT TGC ATT GCA CTA AGT CTT GCA CTT GTC ACA AAC AGT GCA CCT
       10 Rsa I     20              30              40              50              60              70

Thr Ser Ser Thr Lys Lys Thr Gln Leu Gln Leu Glu His Leu Leu Leu Asp Leu Gln Met Ile Leu Asn
           ACT TCA AGT TCT ACA AAG AAA ACA CAG CTA CAA CTG GAG CAT TTA CTG CTG GAT TTA CAG ATG ATT TTG AAT
            80              90             100             110             120             130             140

50                                  60                                         70
           Gly Ile Asn Tyr Lys Asn Pro Lys Leu Thr Arg Met Leu Thr Phe Lys Phe Tyr Met Pro Lys Lys Ala
           GGA ATT AAT TAC AAG AAT CCC AAA CTC ACC AGG ATG CTC ACA TTT AAG TTT TAC ATG CCC AAG AAG GCC
              150             160             170             180             190             200             210

80                                          90
           Thr Glu Leu Lys His Leu Gln Cys Leu Glu Glu Glu Leu Lys Pro Leu Glu Glu Val Leu Asn Leu Ala Gln
           ACA GAA CTG AAA CAT CTT CAG TGT CTA GAA GAA GAA CTC AAA CCT CTG GAG GAA GTG CTA AAT TTA GCT CAA
              220             230             240             250             260             270             280

100                                         110
           Ser Lys Asn Phe His Leu Arg Pro Arg Asp Leu Ile Ser Asn Ile Asn Val Ile Val Leu Glu Leu Lys Gly
           AGC AAA AAC TTT CAC TTA AGA CCC AGG GAC TTA ATC AGC AAT ATC AAC GTA ATA GTT CTG GAA CTA AAG GGA
              290             300             310             320             330             340             350             360
```

FIG. 1A

```
              120                          130                              140
Ser Glu Thr Thr Phe Met Cys Glu Tyr Ala Asp Glu Thr Ala Thr Ile Val Glu Phe Leu Asn Arg Trp Ile
TCT GAA ACA ACA TTC ATG TGT GAA TAT GCT GAT GAG ACA GCA ACC ATT GTA GAA TTT CTG AAC AGA TGG ATT
        370             380             390             400             410             420             430

150             153
Thr Phe Cys Gln Ser Ile Ile Ser Thr Leu Thr End
ACC TTT TGT CAA AGC ATC ATC TCA ACA CTA ACT TGA TAATTAAGTGCTTCCCACTTAAAACATATCAGGCCTTCTATTTAAAA
        440             450             460              470        480         490        510

TATTTAAATTTTATATTTATTGTTGAATGTATGGTTTGCTACCTATTGTAACTATTATTCTTAAATCTTAAAACTATAAATATGGATCTTTATGATTCT
 520        530         540        550         560        570         580        590         610

TTTTGTAAGCCCTAGGGGCTCTAAAATGGTTTCACTTATTTATCCCAAAATATTTATTATTGTTGAATGTTAAATATAGTATCTATGTGATTAGTTAGTAA
 620        630         640        650         660        670         680        690        700        710   720
                                                                                                            Pst I

FIGS. 1A-1B: Nucleotide sequence (upper line) and amino acid sequence (lower line) of
human interleukin 2 (IL-2) gene isolated with synthetic oligonucleotide probe. The
numbers above each line refer to amino acid position beginning at initiator codon ATG and
numbers below each line refer to nucleotide position. The portion of the DNA fragment
used to probe bovine cDNA library is indicated by the solid underlining. Mature protein
begins at asterisk (*).

```
         M              R                                                           B H
         N              S                                                           S G N              A
         L              A                                                           P I S              L
      1  1           20 1                         40                60              I A P              U
                                                                                    1 1             80 2 1        100
CCTCAACTCCTGCCACAATGTACAAGATACAACTCTTGTCTTTGCATTGCACTAACTCGTTGCAAACGGTGCACCTACTTCAAGCTCTACGGG
                      MetTyrLysIleGlnLeuLeuSerCysIleAlaLeuThrLeuAlaLeuValAlaAsnGlyAlaProThrSerSerThrGly
                    1                             10                          20          *
                                    F                                                         S        B S
                                    N                          D                              A F  M   A S C      N
                                 B  U                          D                              L A  N   P T R      S
                              B  B  V  4                       E                              U N  L   Y N F      I
                           1  1  1  1  H                       1                              1 1  1   1 1 1      1
                   120                              140                    160                         180                  200
GAACACAATGAAAGAAGTGAAGTCATTGCTGCTGGATTTACAGTTGCTTTGGAGAAAGTTAAAAATCCTGAGAACCTCAAGCTCTCCAGGATGCATACA
AsnThrMetLysGluValLysSerLeuLeuLeuAspLeuGlnLeuLeuLeuGluLysValLysAsnProGluAsnLeuLysLeuSerArgMetHisThr
         30                         40                         50                         60

B          H                                                                  M  X M                   A
      F  S N S      I H                                             M                  B  B A                   L
      O  P S T      N P                                             A                  O  A E                   U
      K  1 P Y      C A                                             E                  2  1 1                   1
      1  2 2 1 2 2 0 2 1                                            1  260                             280                  300
TTTGACTTTTACGTGCCAAGGTTAACGCTACAGAATTGAAACATCTTAAGTGTTTACTAGAAGAACTCAAACTTCTAGAGGAAGTGCTAAATTAGCTC
PheAspPheTyrValProLysValAsnAlaThrGluLeuLeuLysHisLeuLysCysLeuLeuGluLeuLysLeuGluLeuValLeuAsnLeuAlaPro
                  70                           80                         90
                   320                        340                          360                  380                   400
CAAGCAAAAACCTGAACCCCAGAGAGATCAAGGATTCAATGGACAATATCAAGAGAGAATCGTTTGAACTACAGGATCTGAAACAAGATTCACATGTGA
SerLysAsnLeuAsnProArgGluIleLysAspSerMetAspAsnIleLysArgIleValLeuGluLeuGlnGlySerGluThrArgPheThrCysGlu
                100                          110                         120
```

```
                                                      S
                                                      F
                                                      A         S
                                                      N         BA    D
                                                      1         CU    D
                                                                L3    E
                                                                1A    1
                                                                 /
ATATGATGATGCAACAGTAAACGCTGTAGAATTCTGAACAAATGATTACCTTTGTCAAAGCATCTACTCAACAATGACTTGATCACTAAGTGCCTCT
        420          440           460           480           500
TyrAspAlaThrValAsnAlaValGluPheLeuAsnLysTrpIleThrPheCysGlnSerIleTyrSerThrMetThrEnd
    130                   140                   150

MD          D    S    D                                        M
NR          R    S    R                                        A
LA          A    P    A                                        E
11          1    1    1 540                                 580 3
ATATGATGATGCAACAGCTTTCTATTTATTTAAATATTTAAAATTTATATTTATTTTTGATATATGTTTCCTACCTTTTGTAACTGTTAGTCTTAAGA
    520                    540          560           580          600

S
           AX   H
           UH   I
           30   N
           A2   F
              / 1
CATTTTAAACTATCAGGCTTTCTATTTATTTAAATATTTAAAATTTATATTTATTTTTGATATATGTTTCCTACCTTTTGTAACTGTTAGTCTTAAGA
        520          540           560           580           600

620
TGATAAATATGGATCTTTTAAGATTCTTTTTGTAAGCCCTACTtGGTTcAAAAAaTTCAGTTAAATTATTTATCCTGAAGTATTTtATTTtGTATATTGA
        620          640           660           680           700 aTTTTTTAATATAATGTCTATGCAGGTCATTGACTAAATTATTTATACGTTGATGATAAaCAAa
        720          740           760
```

FIGS. 2A-2B: Nucleotide sequence (upper line) and amino acid sequence (lower line) for bovine plasmid DNA B-IL-2-4 coding for the IL-2 gene. Mature protein begins at asterisk (*). Numbers above each line refer to nucleotide position and numbers below refer to amino acid position beginning at mature protein. Certain restriction enzyme cleavage sites are also indicated.

DNA SEQUENCES ENCODING BOVINE INTERLEUKIN-2

CROSS-REFERENCE TO RELATED APPLICATION

This is a continuation-in-part of copending U.S. patent application Ser. No. 766,643, filed Aug. 16, 1985, now abandoned.

TECHNICAL FIELD

The present invention relates to bovine interleukin-2 (hereafter "bIL-2") and, more particularly, to the cloning of the gene for bIL-2 by use of a probe derived from a human interleukin-2 ("IL-2") complementary deoxyribonucleic acid ("cDNA") clone to screen a cDNA library synthesized from bovine messenger ribonucleic acid ("mRNA") containing bIL-2 mRNA.

BACKGROUND OF THE INVENTION

IL-2 is a soluble protein which is capable of modulating lymphocyte reactivity and promoting the long-term in vitro culture of antigen-specific effector T-lymphocytes (mitogenesis) and, in the past, has been produced by stimulating mouse, rat or human lymphocyte cells with a mitogen. For instance, Morgan et al. in *Science* 193:1007 (1976) and Ruscetti et al. in *J. Immunol.*, 119:131 (1977), both discussed a process for culturing pooled normal human lymphocytes in Roswell Park Memorial Institute -1640 medium (hereinafter "RPMI-1640") containing autologous serum and the mitogen phytohemagglutinin (hereafter "PHA").

Gillis and Smith, in *Nature*, 268:154 (1977) reported preparing murine IL-2 by stimulating normal DBA/2 mouse spleen cells with the mitogen concanavalin A (hereafter "Con A") in an RPMI-1640 culture medium containing fetal calf serum (hereafter "FCS").

Farrar et al. in *J. Immunol.*, 121:1353 (1978), also disclosed preparing IL-2 from murine spleen cells incubated with Con A in a tissue culture medium containing normal mouse serum (hereafter "NMS").

Gillis et al. reported generating IL-2 from murine and rat spleen cells cultured in a RPMI-1640 tissue culture medium supplemented with heat-inactivated FCS, penicillin-G, and gentamicin. The murine and rate spleen cells were stimulated by various mitogens including Con A, PHA, and pokeweed mitogen (hereafter "PKM"), *J. Immunol.*, 120:2027 (1978).

IL-2 also has been prepared from human peripheral blood mononuclear cells by culturing the cells in RPMI-1640 medium supplemented with autologous human serum, penicillin, gentamicin, fresh L-glutamine, and PHA. Gillis et al. in *J. Immunol.*, 124:1954 (1980).

Gillis et al. in *J. Immunol.*, 125:2570 (1980), identified the preparation of IL-2 from T cell leukemia and lumphoma cell lines, specifically a radiation-induced splenic lymphoma from the B10.BR mouse (LBRM-33) cultured in RPMI-1640 supplemented with heat-inactivated FCS, $2.5 \times 10^{-5}$M 2-mercaptoethanol, N-2-hydroxy-piperazine-XI$^1$-2-ethene-sulfonic acid (hereafter "HEPES") buffer, penicillin, streptomycin and fresh L-glutamine. The cultures were stimulated with various mitogens including Con A and PHA.

IL-2 purified from these mouse, rat and human normal T-lymphocytes, has been found to retain different types of biological activity, including: (1) marked enhancement of thymocyte mitogenesis, Watson et al. *J. Exp. Med.*, 150:849 (1979) and Gillis et al. supra, *J. Immunol.*, 124:1954; (2) promotion of long-term in vitro proliferation of antigen specific helper or killer T cell lines, Gillis et al. supra, *Nature*, 268:154 and Watson, *J. Exp. Med.*, 150:1510 (1979); and, (3) induction of cytotoxic T lymphocyte (hereafter "CTL") reactivity and plaque-forming cell responses in cultures of nude mouse spleen cells. Watson et al., supra, *J. Exp. Med.*, 150:849 and Gillis et al., supra, *J. Immunol.*, 124:1954. Accordingly, these identified biological activities of IL-2 indicate that IL-2 is useful in elevating immune responses and restoring immune deficient T Cell populations (nude mouse spleen cells) to normal levels of cell and humoral immunity. Futhermore, these results suggest that IL-2 production and response are important parameters of immunological functions which may be useful in clinical diagnosis of aberrant immunity. Moreover, the fact that human IL-2 makes possible the in vitro proliferation of antigen specific human, mouse and rat killer T cells emphasizes the importance of human IL-2 as a research agent.

For these and similar reasons, human IL-2 is currently being evaluated as therapeutic in human clinical trials. IL-2 is a key regulator of immune function and also may be of value in the treatment of economic animals, particularly in cases of stress-induced immune deficiency of cattle. It has been repeatedly hypothesized that the stress that cattle undergo during shipment to and from grazing areas to feed lots causes elevation in steroid hormone production which leads to a diminution of immune responsiveness. When animals arrive at a feed lot, due to decreased immune reactivity, they fall prey to common bacterial and viral infections which, under normal situatons, such animals have the ability to counteract. Various types of upper respiratory tract infections can occur. The effect of this "shipping fever" syndrome is that animals in such situations go off feed, lose weight, and can even die from these normally rejected disease-causing infectious agents. Gillis and colleagues several years ago showed that steroid hormones dramatically depressed immune responses via their capacity to diminish IL-2 production. In fact, in vitro addition of IL-2 to steroid-suppressed immune responses dramatically restored immune reactivity. Based on these results, it is not surprising to suggest that the use of bIL-2 in the teratment of shipping fever syndrome could result in elimination of the syndrome and restoration of the many millions of dollars which are lost as a result of shipping induced immune deficiencies. Unfortunately, methods for production of bIL-2 are not well characterized. As well, sources of natural bIL-2 have not proven to be a workable system for generating sufficient quantities of homogeneous IL-2 to thoroughly investigate its potential therapeutic usefulness.

One potential method of producing relatively large quantities of homogeneous bIL-2 is through recombinant DNA techniques. Recombinant DNA techniques have been developed for economically producing a desired protein once the gene coding for the protein has been isolated and identified. A discussion of such recombinant DNA techniques for protein production is set forth in the editorial and supporting papers in Volume 196 of *Science* (April, 1977). However, to take advantage of the recombinant DNA techniques discussed in this reference, the gene coding for bIL-2 must first be isolated.

SUMMARY OF THE INVENTION

In accordance with the present invention, the gene coding for bIL-2 is isolated from a cDNA library with a nick-translated human cDNA probe. The probe is isolated from a human cDNA library by use of a synthetic oligonucleotide probe corresponding to a portion of the nucleotide sequence of human IL-2. Total bovine RNA is extracted from lymph node cells known to produce relatively high levels of bIL-2. Polyadenylated mRNA is isolated from the total RNA extract. A cDNA library is constructed by reverse transcription of the polyadenylated mRNA with reverse transcriptase. The DNA is rendered double-stranded with DNA polymersae I and inserted into an appropriate cloning vector. Resultant recombinant cloning vectors are used to transform an appropriate host.

Transformed hosts are identified and grouped into pools. Plasmid DNA prepared from these pools is hybridized with the human cDNA probe that has been radiolabeled. The pool(s) of clones that give a positive signal to the probe are identified and then the putative pool subdivided and the hybridization screen repeated. A single transformant corresponding to the bIL-2 gene is eventually identified. Plasmid DNA is prepared from this transformant and characterized by DNA sequencing. In addition, the corresponding amino acid sequence is determined from the nucleotide sequence. The coding region of the bIL-2 gene is cloned into both yeast and bacterial expression systems to express mature bIL-2. The recombinant bIL-2 (hereinafter "rbIL-2") from the expression systems is purified to homogeneity by reverse phase high-performance liquid chromatography ("HPLC") techniques. Thereafter, biological assays are conducted to confirm that the expressed protein product is bIL-2 and the rbIL-2 is analyzed for amino acid composition and sequence.

BRIEF DESCRIPTION OF THE DRAWINGS

The details of typical embodiments of the present invention will be described in connection with the accompanying drawings, in which:

FIGS. 1A and 1B (hereinafter jointly referred to as "FIG. 1") illustrate the amino acid sequence (upper line) and nucleotide sequence (lower line) of the gene coding for human IL-2;

FIGS. 2A and 2B (hereinafter jointly referred to as "FIG. 2") illustrate the amino acid sequence (lower line) and nucleotide sequence (upper line) of the bIL-2 gene, with the mature protein beginning at the asterisk;

FIG. 5B sets forth the analysis of aliquots from the same fractions for the presence of biological activity in a bIL-2 dependent T-cell proliferation assay.

FIG. 6A shows the results of polyacrylamide gel electrophoresis of active fractions recovered from the second HPLC column. The numbers below the lanes corresponding to the fractions eluted from the second column and molecular weight markers are indicated adjacent to the first column (left-hand side). FIG. 6B illustrates the results of biological assay of the homogeneous rbIL-2 from the same fractions shown in FIG. 6A.

DESCRIPTION OF THE INVENTION

Sources of bIL-2 Producing Cells

Figure 3:
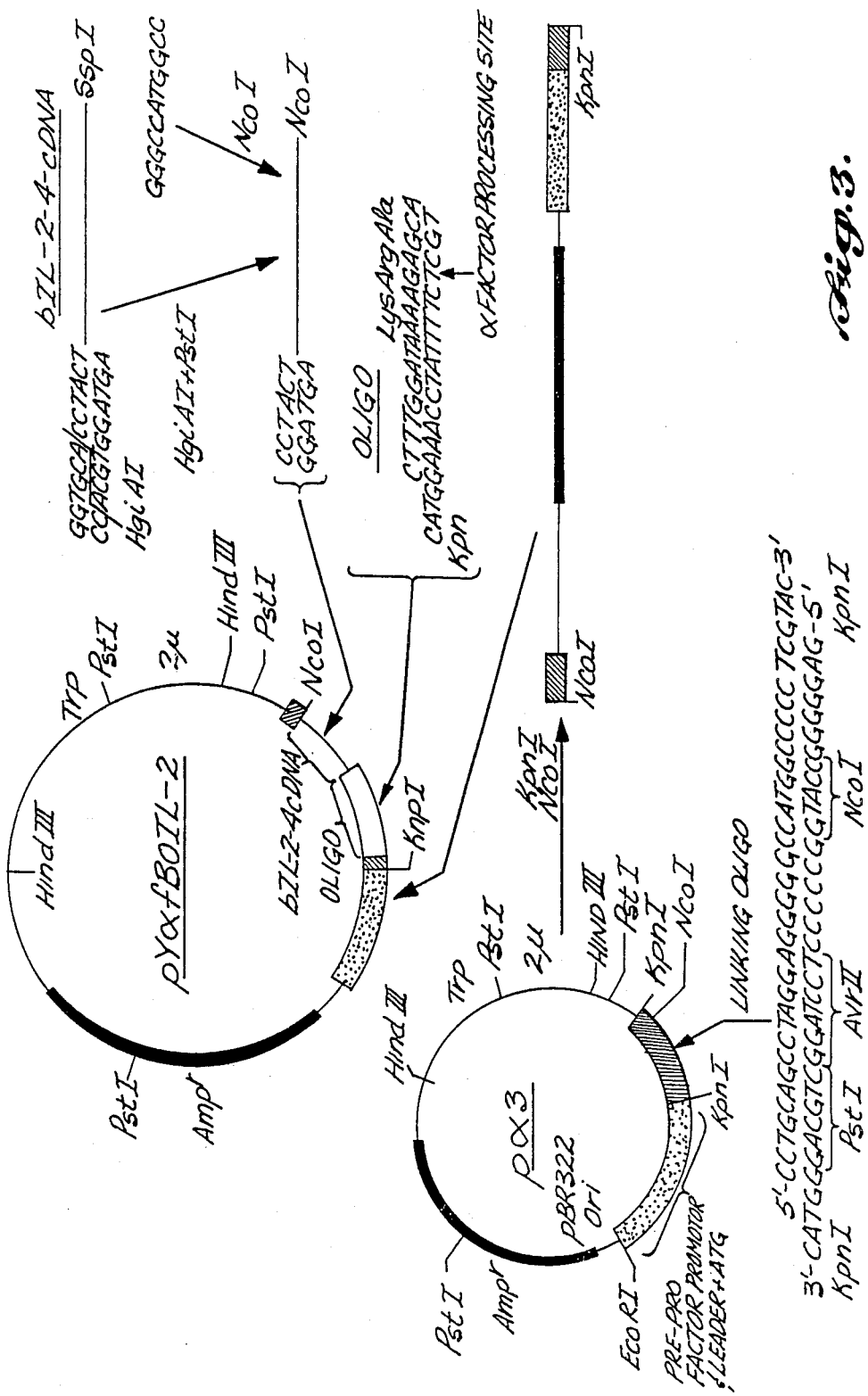
FIG. 3 illustrates the strategy employed to construct the pYαfBoIL-2 plasmid, with the coding region of the bIL-2 gene inserted therein, for use in transforming yeast host cells to express functional bIL-2.

Preferably, a cDNA library, from which the gene coding for bIL-2 will be sought, is constructed from cells previously found to produce relatively high levels of bIL-2. These sources may include any source of bovine T-cell tissue, i.e., lymph node or spleen.

Activated bovine peripheral blood also potentially may be a source of bIL-2 molecules. For use in the present invention, the mononuclear cells can be separated from whole blood by standard techniques, such as by Ficoll-Hypaque centrifugation. Harvested leukocytes are multiplied by culturing in vitro in a serum containing medium together with a T-cell mitogen. As set forth infra, applicants have successfully isolated the bIL-2 gene from a cDNA library prepared from mitogen stimulated bovine peripheral blood cells.

Preparation of RNA from bIL-2 Producing Cells

Total RNA from bovine, potentially IL-2 producing cells is extracted by standard methods, such as disclosed by Chirgwin et al., *Biochemistry*, 18:5294 (1979), and Maniatis et al., *Molecular Cloning, a Laboratory Manual*, Cold Spring Harbor Laboratory, Cold Spring Harbor, N.Y. (1982).

As is well known, when extracting RNA from cells, it is important to minimize ribonuclease ("RNase") activity during the initial stages of extraction. One manner in which this is accomplished is to denature the cellular protein, including the RNase, at a rate that exceeds the rate of RNA hydrolysis by RNase. In the procedures of Chirgwin et al., spura, and Maniatis et al., supra at 196, this is carried out by use of guanidinium thiocyanate, together with a reducing agent, such as 2- mercaptoethanol (to break up the protein disulfide bonds). The RNA is isolated from the protein by standard techniques, such as phenol/chloroform extraction, ethanol precipitation or sedimentation through cesium chloride. Alternatively, the RNA can be separated from the protein by extraction with guanidine hydrochloride followed by extraction with phenol/chloroform.

Next, polyadenylated mRNA is separated from the extracted protein. Although several techniques have been developed to carry out this separation process, one preferred method is to chromatograph the polyadenylated mRNA on oligo (dT)-cellulose as described by Edmonds et al., *Proc. Natl. Acad. Sci.*, 68:1336 (1971); Aviv and Leder, *Proc. Natl. Acad. Sci.*, 69:1408 (1972); and Maniatis et al., supra at 197. The oligo (dT)-cellulose column is prepared with a loading buffer and then the mRNA applied to the column. Thereafter, the column is initially washed with a buffer solution to remove the unpolyadenylated mRNA and then the polyadenylated mRNA is eluted from the column with a buffered, low ionic strength eluant. The integrity of the polyadenylated mRNA is verified by gel electrophoresis.

Preparation of cDNA from mRNA

A library of double-stranded cDNA corresponding to the mRNA, as prepared and assayed above, is constructed by known techniques employing the enzyme reverse transcriptase. One such procedure which may be employed in conjunction with the present invention is detailed by Maniatis et al., supra at 230, as modified by Gubler and Hoffman, *Gene,* 25:263-269 (1983). Briefly, the polyadenylated mRNA is reverse transcribed by using oligo-dT, that has been hybridized to the polyadenylated tail of the mRNA, as a primer for a first cDNA strand. The second cDNA strand is synthesized using the enzymes DNA polymerase I, RNase H and *E. coli* DNA ligase. This procedure eliminates the S1 nuclease mediated cleaving of the hairpin loop formed in the 3' end of the initial cDNA strand, as would be required if standard cDNA synthesis techniques disclosed in Maniatis et al. supra, were simply used. The double-stranded cDNA is fractionated by any convenient means to remove the shorter strands, thereby avoiding the needless cloning of small cDNA fractions.

It is to be understood that in accordance with the present invention, alternative standard procedures may be employed to prepare double-stranded cDNA from mRNA. One such alternative technique is disclosed by Land et al., *Nucl. Acids Res.,* 9:2251 (1981). In the Land et al. protocol, the hairpin loop also is not used as a primer for the second cDNA strand. Rather, the 3' end of the first cDNA strand is tailed with dCMP residues using terminal deoxynucleotidyl transferase ("TdT"). This produces a 3' tail of poly-C residues. Then the synthesis of the second strand is primed by oligo-dG hybridized to the 3' tail. This technique is said to help avoid losing portions of the 5' tail of the second cDNA strand which might occur if the hairpin is cleaved with S1 nuclease, as in the Maniatis et al. protocol.

Cloning of cDNA

Next, the double-stranded cDNA is inserted within a cloning vector which is used to transform compatible prokaryotic or eukaryotic host cells for replication of the vector. Thereafter, the transformants are identified and plasmid DNA prepared therefrom.

To carry out the present invention, various cloning vectors may be utilized. Although the preference is for a plasmid, the vector may be a bacteriophage or a cosmid. If cloning occurs in mammalian cells, viruses also can be used as vectors.

If a plasmid is employed, it may be obtained from a natural source or artificially synthesized. The particular plasmid chosen should be compatible with the contemplated transformation host, whether a bacterial such as *E. coli,* yeast, or other unicellular microorganism. The plasmid should have the proper origin of replication for the particular host cell to be employed. Also, the plasmid should have a phenotypic property that will enable the transformed host cells to be readily identified and separated from cells that do not undergo transformation. Such phenotypic characteristics can include genes providing resistance to growth inhibiting substances, such as an antibiotic. Plasmids are commercially available that encode genes resistant to various antibiotics, including tetracycline, streptomycin, sulfa drugs, penicillin and ampicillin.

If *E. coli* is employed as the host cell, many possible cloning plasmids are commercially available which may be used in conjunction with the present invention. A preferred plasmid for performing the present invention is pBR322. This plasmid has been fully sequenced, as set forth in Sutcliffe, *Cold Spring Harbor Symp. Quant. Biol.,* 43:77 (1979). A significant advantage of this plasmid is that it has 11 known unique restriction sites, including the Pst I site in the ampicillin-resistant gene. This feature is particularly useful for cloning by the homopolymer tailing method.

If a bacteriophage is used instead of a plasmid, such phages should have substantially the same characteristics noted above for selection of plasmids. This includes the existence of a phenotypic marker and ligatable termini for attachment of foreign genes.

Preferably, in the present invention, the double-stranded cDNA, having blunt ends, may be inserted into a plasmid vector by homopolymeric tailing. As is well known in the art, in this technique, complementary homopolymer tracks are added to the strands of the cDNA and to the plasmid DNA. The vector and double-stranded cDNA are then joined together by hydrogen bonding between complementary homopolymeric tails to form open, circular hybrid molecules capable of transforming host cells, such as *E. coli.*

In one procedure for homopolymeric tailing, approximately 50 to 150 dA nucleotide residues are added to the 3' ends of linearized plasmid DNA. A similar number of dT nucleotide residues are added to the 3' ends of the double-stranded cDNA and then the cDNA and plasmid joined together.

In an alternative and preferred method, dG tails are added to the 3' ends of the cloning vector that has been cleaved with an appropriate restriction enzyme. For instance, if the pBR322 plasmid is employed, the restriction enzyme Pst I may be used to digest the plasmid at the ampicillin resistant gene. Complementary dC tails are added to the 3' ends of the double-stranded cDNA prior to insertion of the cDNA segment in the plasmid with an appropriate annealing buffer.

It is to be understood that the double-stranded cDNA may be inserted within plasmid cloning vectors by other various standard methods. One such alternative technique involves attaching synthesized nucleotide linkers to the ends of the cDNA strands by using DNA ligase. The linkers are cleaved with a restriction enzyme to generate cohesive termini for insertion within a plasmid cleaved with the same restriction enzyme. Scheller et al., *Science,* 196:177-180 (1977); Maniatis et al., supra at 219.

The recombinant DNA plasmids, as prepared above, are used to transform host cells. Although the host may be any appropriate prokaryotic or eukaryotic cell, it is preferably a well-defined bacteria, such as *E. coli* or a yeast strain. Such hosts are readily transformed and capable of rapid growth in culture. Other forms of bacteria, such as salmonella or pneumococcus, may be substituted for *E. coli.* In place of bacteria, other unicellular microorganisms may be employed, for instance, fungi and algae. Whatever host is chosen, it should not contain a restriction enzyme that would cleave the recombinant plasmid.

If *E. coli* is employed as a host, preferable strains are MM294 and RR1. Protocols for transformation of the MM294 host by a plasmid vector are well known, as set forth in Maniatis et al., supra at 255; and, Hanahan, *J. Mol. Biol.*, 166:557 (1983). Protocols for transformation of the RR1 host by a plasmid vector are also well known as set forth in Bolivar et al., *Gene*, 2:95 (1977) and Peacock et al., *Biochem. Biophys. Acta.*, 655:243 (1981). Other strains of *E. coli* which also could serve as suitable hosts include DH1 (American Type Culture Collection, 12301 Parklawn Drive, Rockville, Md. 20852, U.S.A. ["ATCC"] No. 33849) and C600. These strains and the MM294 and RR1 strains are widely commercially available.

In transformation protocols, including those disclosed by Maniatis et al., supra, and Hanahan, supra, only a small portion of the host cells are actually transformed, due to limited plasmid uptake by the cells. The cells that have been transformed can be identified by placing the cell culture on agar plates containing suitable growth medium and a phenotypic identifier, such as an antibiotic. Only those cells that have the proper resistance gene (e.g., to the antibiotic) will survive. If the recombinant pBR322 plasmid is used to transform *E. coli* strain MM294, transformed cells can be identified by using tetracycline as the phenotypic identifier.

Preparation of Radiolabeled cDNA Screening Probe

A radiolabeled DNA fragment composed of several hundred basepairs ("bp") corresponding to a majority of the nucleotide sequence of the gene coding for the human IL-2 species is used as a probe to screen the above-prepared bovine cDNA library. The probe is isolated from a human cDNA library with a radiolabeled, synthetic oligonucleotide probe corresponding to a portion of the nucleotide sequence of human IL-2.

To isolate the cDNA probe for use in the screening procedure of the present invention, a human cDNA library is initially prepared from human mRNA using the procedures set forth above. The mRNA is extracted from a human cell line known to produce IL-2. Such cell lines may include various T cell lines, such as the T-leukemia cell line Jurkat or clones thereof. This cell line and clones thereof have been extensively used by U.S. and foreign researchers and are available from a wide variety of commercial and private sources, such as from the ATCC. Total RNA from the human cells is extracted by standard methods as discussed above, for instance, by the use of guanidinium thiocyanate together with 2-mercaptoethanol. Thereafter, polyadenylated mRNA is separated from the extracted protein by chromatography on oligo (dT)-cellulose.

A library of double-stranded cDNA corresponding to the human mRNA is constructed, as discussed above, by employing reverse transcriptase to form an initial cDNA strand by using the mRNA as a template. Next, the enzyme DNA polymerase I is used to synthesize the second cDNA strand, employing the first strand as a template. The double-stranded cDNA is inserted within a cloning vector which is used to transform compatible host cells for replication of the vector. Preferably, the vector is composed of a plasmid having a number of unique restriction sites, such as the plasmid pBR322. The cDNA prepared from the mRNA may be inserted within this plasmid by homopolymeric tailing, as described above. The recombinant plasmids are used to transform a compatible host, such as a strain of *E. coli*. Of course, other appropriate hosts may be employed. The host cells that are transformed by the recombinant plasmid are identified with an appropriate standard phenotypic identifier, such as an antibiotic.

A radiolabeled oligonucleotide is synthesized for use as a probe to screen the human cDNA library. The probe, derived of a portion of the antisense strand of the gene coding for human IL-2, has the following composition: 5'-AA TGT GAG CAT CCT GGT GAG-3'. This probe complements the nucleotides 173 through 192 of the sense strand shown in FIG. 1, and has the advantage of being short enough to be relatively easily synthesized, while being long enough to contain sufficient information to be useful as a probe for the human IL-2 gene. It is to be understood, however, that the composition of the probe may correspond to other portions of the human IL-2 gene without departing from the scope or spirit of the present invention.

The synthetic oligonucleotide probe may be readily chemically synthesized by well-known techniques, such as by phosphodiester or triester methods. The details of the triester synthesis technique are set forth, for example, in Sood et al., *Nucl. Acid Res.*, 4:2557 (1977); and, Hirose et al., *Tet. Lett.*, 28:2449 (1978). After synthesis, the oligonucleotide probe is labeled with T4 polynucleotide kinase and $^{32}$P-ATP. A standard protocol for the labeling procedure is set forth in Maniatis et al., supra at 122. Advantageously, the oligonucleotide probe can be synthesized with OH 5' termini, thereby avoiding the phosphatase procedure typically required.

The human cDNA library is screened with the synthetic radiolabeled probe as detailed infra, for example, in Examples 3 and 4. Plasmid DNA is then prepared from the particular positive colony identified by the screening procedure.

The human plasmid DNA is sequenced by the chain-termination method discussed infra. From the sequencing results, as shown in FIG. 1, the isolated plasmid DNA was found to include substantially the entire coding region of the human IL-2 gene.

Essentially the entire length of the isolated human plasmid DNA was chosen as a probe for screening the bovine cDNA library prepared above. A relatively large size probe (in the range of 300–500 bp) usually increases the likelihood that cDNA, actually coding for bIL-2 would be hybridized rather than non-IL-2 coding cDNA fragments. As detailed below, use of this probe was successful in isolating the bIL-2 gene from a cDNA library. It is to be understood that probes corresponding to other portions of the nucleotide sequence of the human plasmid DNA fragment may be employed without departing from the spirit or scope of the present invention.

The human cDNA probe is radiolabeled prior to being used for hybridizing to the bovine cDNA library pools. Due to the relative large size of the probe, various labeling techniques may be employed; however, preferably the probe is labeled by "nick translation." In this well-known technique, as discussed by Rigby et al., *J. Molec. Bio..*, 113:237 (1977), and Maniatis et al., supra at 108, nicks are introduced at widely separated sites in the DNA by very limited treatment with DNase I, thereby exposing a free 3'-OH group at each nick. DNA polymerasae I is employed to incorporate appropriate radiolabeled deoxynucleotide triphosphates ($^{32}$P-dNTPs), at the 3'-OH terminus and concurrently remove the nucleotide from the 5' side of the nick causing sequential movement of the nick along the DNA ("nick translation").

Screening of cDNA Library

In the screening procedure of the present invention, the transformants are initially pooled into relatively large groups each composed of approximately 2,500 transformants. The replicated plasmids are extracted from the transformants using any one of several well-known techniques, such as by alkaline lysis. Plasmid DNA is prepared by cleaving the extracted plasmids with Pst I. The resulting DNA segments are fractionated by electrophoresis on agarose gels and then directly analyzed by Southern blotting as described by Southern, *J. Mol. Biol.*, 98:503 (1975). The DNA fragments that bind to the nitrocellulose filter in the Southern blotting procedure are hybridized with the labeled cDNA probe. The specific DNA fragments that hybridize to the probe are identified by autoradiography.

The putative pool(s) of clones that discloses a strongly hybridizing band during autoradiography is subdivided into groups of approximately 500 transformants, and then the above-described hybridizing screen using the labeled cDNA probe is repeated. This process of subdividing putative pools of clones and screening transformants is repeated until a desired pool size is obtained. A single transformant that hybridizes to the labeled probe is then identified by the well-known colony hybridizing technique of Grunstein and Hogness, *Proc. Natl. Acad. Sci. (U.S.A.)*, 72:3961 (1975). By this procedure, applicants have discovered one such positive colony. Plasmid DNA, designated as B-IL-2-4, is prepared from this particular colony.

Characterization of Screened cDNA

The plasmid DNA prepared above is sequenced using standard chain-termination methods. This technique of nucleotide sequencing was originated by Sanger et al., *Proc. Natl. Acad. Sci. (U.S.A.)* 70:5463 (1977). See U.S. Pat. No. 4,322,499. Methods for chain-termination sequence determination are set forth in the Amersham Handbook entitled, *M13 Cloning and Sequencing*, Blenheim Cresent, London (1983) (hereinafter "Amersham Handbook"); Messing, *Recombinant DNA Technical Bulletin, NIH Publication No. 79-99*, 2, 43-48 (1979); Norrander et al., *Gene* 26:101 (1983); Cerretti et al., *Nucl. Acids Res.*, 11:2599 (1983); and, Biggin et al., *Proc. Natl. Acad. Sci. (U.S.A.)*, 80:3963 (1983). M13 filamentous phage is employed as a vector to clone the DNA sequence of interest. These phage vectors provide single-stranded DNA templates which are readily sequenced by the chain-termination method, which involves priming a single-straned template molecule with a short primer strand having a free 3' hydroxyl group and then using DNA polymerase (Klenow fragment) to copy the template strand in a chain extension reaction using all four deoxyribonucleotide triphosphates, i.e., dATP, dCTP, dGTP, and dTTP (collectively referred to as "dNTPs"), with one of the dNTPs being radiolabeled. In the synthesis reaction, a nucleotide specific chain terminator lacking a 3'-hydroxyl terminus, for instance, a 2', 3' dideoxynucleotide triphosphate ("ddNTP"), is used to produce a series of different length chain extensions. The terminator has a normal 5' terminus so that it can be incorporated into a growing DNA chain, but lacks a 3' hydroxyl terminus. Once the terminator has been integrated into a DNA chain, no further deoxynucleotide triphosphates can be added so that growth of the chain stops. Four separate synthesizing reactions are carried out, each having a ddNTP of one of the four nucleotide dNPTs, i.e., dATP, dCPT, dGTP, and dTTP. One of the normal dNTPs is radiolabeled so that the synthesized strands, after having been sorted by size on a polyacrylamide gel, can be autoradiographed. The chain extensions from the four reactions are placed side by side in separate gel lanes so that the pattern of the fragments from the autoradiography corresponds to the nucleic acid sequence of the cloned DNA.

FIG. 2 illustrates the nucleotide sequence of the bIL-2 gene contained in the B-IL-2-4 plasmid DNA prepared above with the nucleotides numbered from the beginning of the 5' terminal. The corresponding amino acid composition of the gene is also illustrated in FIG. 2, with the residues numbered from the beginning of the coding region of the gene (nucleotide No. 18). The mature protein begins at the Ala residue, No. 21 (nucleotide No. 78), indicated with an asterisk, and extends to the Thr residue, No. 155 (nucleotide No. 482).

In preparation for the sequencing procedures, the plasmid DNA containing the DNA insert is subcloned into M13 phage vectors to form single stranded DNA templates. A universal primer is used to sequence the sense and antisense strands. Rather than relying on the sequencing results obtained from sequencing the entire length of the fragments with a single chain-termination procedure, an additional synthetically produced primer is used to initiate the chain-termination procedure from an intermediate location along the length of the subcloned DNA fragment. The composition of the synthetically produced primer was based on the sequence information obtained using the universal primer. By this process, both strands of the subcloned DNA fragment are sequenced in overlapping fashion, thereby serving to redundantly confirm the sequences.

It is to be understood that rather than employing the chain-termination technique outlined above, other known methods may be utilized to sequence cloned bovine cDNA inserts without departing from the spirit or scope of the present invention. For instance, the chemical degradation method of Maxam and Gilbert as set forth in *Proc. Natl Acad. Sci. (U.S.A.)*, 74:560 (1977) can be used.

Expression of Functional bIL-2 from cDNA Clones

To determine whether the cDNA coding region of the bIL-2 gene as contained in plasmid bIL-2-4 would encode functional bIL-2, the gene is expressed in yeast and bacteria expression systems and then tested for its ability to support growth of IL-2 dependent bovine T-cells.

Expression in Yeast System

A cDNA fragment of substantially the entire coding region of the bIL-2 is inserted into an expression vector, FIG. 3, designed to direct synthesis and secretion of the mature form of bIL-2 from yeast host cells. The expression vector, for instance vector pYαfBoIL-2, preferably contains sequences derived from plasmid pBR332 containing an origin of replication and the ampicillin resistance gene (AMP$^r$) (thick line portion in FIG. 3). Preferably the expression vector also includes sequences from yeast, for instance, the tryptophan-1 gene (Trp-1) as a selectable marker and the 2u yeast origin of replication (thin line portion in FIG. 3). Ideally the expression vector further includes the yeast α-factor (for instance stippled box portion in FIG. 3) as an efficient promoter together with leader sequences to direct the synthesis and secretion of bIL-2 in yeast hosts, followed by the methods as detailed by Sood et al., supra and Hirose et al., supra, or by phosphodiester methods.

TABLE 1

```
                                              Met Ala
5'-CTAG AGG ATC CTA AGT AAG GAG GTT TAA CCC ATG GCA -3'
3'-     TCC TAG GAT TCA TTC CTC CAA ATT GGG TAC CGT -5'
Xba I
``` sequence for the coding region of bIL-2 (hatched box portion). The structure of the α-factor gene is discussed in Kurjan and Herskowitz, *Cell*, 30:933–943 (1982).

The expression plasmid is then transformed into an appropriate strain of *Saccharomyces cerevisiae* ("*S. cerevisiae*"). Preferable strains include, but are not limited to, yeast strains 79, X2181–1B, DBY746, YNN282, 20B-12, XV2181. These strains are all α, Trp 1, Leu 2 for compatability with the α-factor promoter and for selection of Trp+ transformants. These strains are all widely available, for instance strain 79 is available from the Yeast Genetic Stock Center, Department of BioPhysics and Medical Physics, University of Calif., Berkeley, Calif. 94702.

Transformation of the yeast host with the recombinant expression plasmid containing the bIL-2 gene is conducted according to well-known procedures wherein spheroplasts are formed and then washed prior to plasmid uptake. Standard protocols for this procedure have been established. See Beggs, *Nature (London)*, 275:104 (1978); and, Hinnen et al., *Proc. Natl. Acad. Sci. (U.S.A.)*, 75:1929 (1978).

The yeast culture supernatants are assayed for biological activity through their ability to support growth of IL-2 dependent bovine T-cells. Details of the bIL-2 activity assay are set forth below. In the assay, the yeast supernatant was found to exhibit relatively high levels of bIL-2 activity. As a control, plasmid of the same construction as the expression plasmid but lacking the bIL-2 sequences was also transformed into a yeast host; upon assay, no biological activity was detected from the supernatant derived from the control plasmid.

Expression in Bacteria Host cDNA fragments of substantially the entire coding region of the bIL-2 gene are also inserted into an expression vector designed to direct synthesis of the mature form of bIL-2 from bacteria host cells. Preferably, but not essentially, the plasmid employed for expression in bacteria cells contains the λ phage $P_L$ promoter. Correspondingly, ideally the bacteria host, for instance, *E. coli* contains a thermolabile cI repressor of $P_L$ transcription. In addition, if *E. coli* is employed as the host, preferably the expression vector contains an origin of replication, for example from plasmid pBR332, for high copy DNA replication and an ampicillin resistant gene ("AMP$^r$"), also from plasmid pBR332 for convenient selection of transformed *E. coli* hosts. Examples of expression vectors meeting these requirements include: plasmid pPL-λ (Pharmacia Fine Chemicals, Cat. No. 27-4946-01); and, plasmid pPLc28 (ATTC No. 53082).

To enhance the level of expressed bIL-2, a highly efficient synthetic translation initiation sequence is employed upstream from the bIL-2 cDNA. The same translation initiation sequence has been used for expression of human IL-2, Marquis, et. al., *J. Cell. Biochem. Supplement*, 9B:221 (1985). The high level translation initiation sequences are incorporated in a synthetic oligonucleotide set forth in TABLE 1 below. The synthetic oligonucleotide may be synthesized by triester As illustrated in TABLE 1, the synthetic oligonucleotide is constructed with a cohesive Xba I 5' end and a blunt 3' end which contains the initiation codon ATG and sequences encoding the first amino acid residue Ala of the mature bIL-2 protein. The intermediate portion of the oligonucleotide between the Xba I restriction site and the Met initiation codon composes the translation initiation sequences. It is to be understood that the 5' terminus and the intermediate portion of the oligonucleotide may be of various compositions to correspond with the construction of the particular plasmid in which the oligonucleotide, together with the bIL-2 gene, is being ligated.

After transformation of the bacteria hosts with the bIL-2 gene containing expression vector, and upon heat induction, high level expression of bIL-2 was confirmed with the bIL-2 dependent cell assay, detailed below. The high assay levels of the recombinant DNA product expressed by both the yeast and bacteria hosts confirm that the gene isolated by applicants, as set forth in FIG. 2, coincides with the bIL-2 gene.

Purification of rbIL-2

The rbIL-2 produced in the yeast and bacterial host expression systems in purified by HPLC. The HPLC columns employed in the present invention preferably utilize a reverse phase, octadecyl bonded silica column having a pore size sufficiently large to be optimally utilized with the proteinaceous rbIL-2, i.e., a pore size of about 15–20 microns.

Suitable reverse phase HPLC columns for use in the practice of the present invention are articles of commerce. Preferred columns include the PrepPAK, ® Radiopak, ® and Porasil, ® lines of columns commercially available from Waters Associates of Milford, Me. Preferable column packing materials include octadecyl silane groups covalently bonded, for instance by means of a siloxane (silicone-oxygen-silicone) bond, to the surface of the silica gel. An example of ths type of packing material is Vydac, ® C-4 (Separations Group, Hesperia, Calif.).

Prior to their application to the column, the expression extracts are diluted, if required, and the column is equilibrated with an appropriate buffer solution, for instance composed of trifluoroacetic acid (TFA) heptafluorobutyric acid (HFBA) or acetic acid. The elution of the proteins from the HPLC column is carried out in a manner well known in the art. Suitable elution procedures for removing the bonded proteins from the column may involve the use of a linear gradient, for instance acetonitrile or an N-propanol buffer solution in TFA, HFBA or acetic acid. If acetonitrile is used as an eluant, a preferred gradient is composed of 0–100% (vol./vol.) of acetonitrile in about 0.05 to 2% TFA which is applied to the column at a rate of approximately 1–3% acetonitrile per minute. If the eluant is composed of an N-propanol buffer solution, a preferred composition is approximately 60% (vol./vol.) N-propanol in 0.9 M acetic acid and 0.2 M pyridine (pH4.0). A preferred gradient range for this buffer eluant is from 0-100% and, more preferably, from 20-80%.

The eluted protein can be conveniently monitored with detection systems that are well known in the art. For example, an automated fluorescence detection system, as described by Stein and Moschera in *Meth. Enzymol.*, 78:435 (1981), may be employed. Alternatively, the relative protein concentrations of the fractions collected from the HPLC columns can be determined by measuring absorbance of the eluted material in an ultraviolet light spectrophotometer, at 280 nanometers (nm) light wavelength. Suitable automated ultraviolet light absorbance detection apparatuses are articles of commerce. For instance they are commercially available from Waters Associates and from LKB Instruments, Inc. of Cambridge, England.

The biological activities of the recovered HPLC fractions are analyzed by the bIL-2 dependent T-cell proliferation assay discussed infra. The fractions are also analyzed by gel electrophoresis.

If sufficient protein purification is not achieved by the initial HPLC procedure, it can be repeated by use of the same column or another column, for instance, a column employing a packing material having a different composition or shape of support material or different chemical composition of the bonded phase material. In addition, the same or different type of eluant may be employed.

If sufficient protein purification does not result from the second HPLC procedure, a third, or further, procedure may be used so that homogeneity is achieved. Applicants have found from gel electrophoresis and biological assay that although the first HPLC treatment with a C14 bonded phase and elution with acetonitrile resulted in substantial purification of the rbIL-2, the protein product was not purified to homogeneity, see FIG. 5. However, after a second HPLC treatment employing the same column as above but with an N-propanol/acetic acid/pyridine eluant, homogeneous bIL-2 was recovered in a single fraction having a molecular weight of approximately 16,000 daltons.

The homogeneous rbIL-2 activity of the present invention was found to be stable for at least 6 months when stored at 4° C. in organic buffers used in HPLC fractionation, supra, (TFA/acetonitrile) or (pyridine/acetate/propanol).

Amino Acid Analysis

The ability to achieve homogeneity of the rbIL-2 has permitted applicants to analyze its amino acid composition and the amino acid sequence of the N-terminal portion of this recombinant protein product. This information in useful in confirming that the expressed product is of the same composition as the natural product and that the expressed product corresponds with the amino acid composition and sequence as prediction from analysis of the rbIL-2 cDNA.

Samples of the homogeneous rbIL-2 of the present invention as prepared above can be analyzed for amino acid composition and sequence, for instance with an automated analysis equipment employing either ninhydrin or gas phase detection. Such equipment are articles of commerce, for example, they are available from LKB, Cambridge, England (Model 4150 Alpha) or from Applied Biosystems (Model 470A). Through this analysis, applicants have found that the amino acid composition of the rbIL-2 corresponds to that predicted from the rbIL-2 cDNA and also that the first 20 residues of the amino terminal portion of the rbIL-2 were the same as the corresponding sequence predicted from the cDNA, i.e., amino acid residue Nos. 21-41 in FIG. 2.

Therapeutic Applications

As discussed above, rbIL-2 prepared in accordance with the present invention may be employed to treat communicable diseases of cattle and other animals, such as mastisis, respiratory and gastro-intestinal syndromes, as well as generalized parasitic infections. Applicants have ascertained that the specific activity of rbIL-2 is approximately $4.5 \times 10^4$ units per microgram ($\mu$g) of protein. For treatment of animal disease, preferable dosages of rIL-2 are in the range of about $10^4$–$10^8$ units per kilogram (kg) of animal weight per dose. rbIL-2 treatment in dosages in the range of 0.1–10 milligrams (mg) and ideally about 5 to 6 mg would be expected to restore T cell-mediated functions in a 1,200 pound cow. To be therapeutically effective, multiple doses of rbIL-2 may likely be required and are within the scope of the present invention.

The rbIL-2 may be administered to cattle by any convenient method, including parenterally or transdermally. For parenteral administration, solutions of the rbIL-2 in sesame or peanut oil or in aqueous propylene glycol may be employed, as well as sterile nontoxic, nonallergic solutions of distilled water, serum albumen, Ringer's solution, Hank's solution, etc. Such solutions could be suitably buffered if necessary and the liquid diluent first rendered isotonic with sufficient saline or glucose. These particular aqueous solutions are specially suitable for intravenous, intramuscular or subcutaneously injection purposes. These various sterile aqueous media are all readily preparable by standard techniques well known to those skilled in the art.

Assay for bIL-2 Activity

As noted above, the expression products from the yeast and bacteria systems discussed above, is assayed with IL-2 dependent bovine T-cells. Details of this type of assay are discussed in Baker and Knoblock, *Vet. Immunol. Immunopath*, 3:381 (1982); Miller-Edge and Splitter, *Vet. Immunol. Immunopath*, 7:119 (1984); Namer and Magnuson, *Immunol.*, 52:469 (1984); Oldham and Williams, *Vet. Immunol. Immunopath*, 1:201 (1984). Briefly in the assay, the IL-2 dependent cells are harvested from culture, washed free of growth medium, and resuspended in complete RPMI-1640 medium at a concentration of $8 \times 10^4$ cells/ml. The cell suspension (100 microliter ($\mu$l)) is placed in individual wells of 96-well microtiter plates (Cat. No. 3596, Costar) followed by serial ($\log_2$) dilutions of samples or a 1 unit/ml monkey IL-2 standard (100 $\mu$l). Microplates are incubated for 48 hours at 37° C. in a humidified atmosphere of 5% $CO_2$ in air. Each well is then pulsed with 50 $\mu$l of medium containing $10^2 \mu$Ci/ml tritiated thymidine ("[$^3$H]-Tdr") (specific activity, 1.9 Ci/mM). The plates are reincubated for an additional 4 hours prior to harvesting with an automated sample harvester. Glass fiber filter strips containing ($^3$H)-Tdr-labeled well contents are air-dried, placed into a toluene-base cocktail (Cat. No. NEF-903, New England Nuclear, Boston, MA), and counted for 0.5 minutes in a liquid scintillation counter.

In the presence of bIL-2, target IL-2 dependent cells incorporate ($^3$H)-Tdr in a dose-dependent manner. In the absence of bIL-2, the target IL-2 dependent cells die within 24 hours and incorporate only background levels of ($^3$H)-Tdr. Units/ml of bIL-2 activity are quantified by determining the dilution at which a particular sample caused half-maximal target cell line proliferation. For example, if a sample generated half-maximal target cell line proliferation in a particular bIL-2 assay (200 μl total volume) at a dilution 1:10, one unit would be said to be contained in a 200 μl (total volume) divided by 10, or 20 μl. The sample would then have a titer of 1,000 (uμin 1 ml) divided by 20 (μin 1 unit), or 50 units/ml.

As noted above, recombinant bIL-2 from the yeast cultures exhibited bIL-2 activity at a level of $1.3 \times 10^6$ units per milliliter. Also, the expression product recovered from the bacteria system exhibited bIL-2 activity at a level of over $10.2 \times 10^6$ units per milliliter thereby confirming that the gene assayed by applicant as set forth in FIG. 2 is in fact a bIL-2 gene.

Analysis of mRNA

The expression of bIL-2 nRNA from bovine lymph node cells was analyzed. Northern blots of RNA from Con A-stimulated and unstimulated bovine lymph node cells were analyzed by hybridization with an RNA probe derived from the bIL-2 cDNA illustrated in FIG. 2. The probe strongly hybridized to a single band of RNA derived from bovine lymph node cells activated with Con A, but no hybridization occurred in RNA from unstimulated lymph node cells.

Analysis of Bovine Genomic Sequences

The number of IL-2 related genes in bovine genomic DNA was investigated by hybridizing a $^{32}$P-labeled bIL-2 probe to Southern blots of bovine genomic DNA fragments. The fragments were prepared by digesting bovine genomic DNA with a number of different restriction enzymes expected to cut the DNA relatively infrequently. Autoradiographs of hybridizations with the IL-2 cDNA probe to Southern blots of genomic DNA indicated that the gene for bIL-2 exists as a single copy.

The processes and products of the present invention are further illustrated by the following examples. The examples are merely exemplary; they are presented to illustrate the present invention and to assist one of ordinary skill in making and using the same. The examples are not intended to limit in any way the scope of the disclosure of claims set forth below for the protection granted by Letters Patent herein.

EXAMPLE 1

Preparation of Polyadenylated mRNA

Bovine peripheral blood leukocytes at a concentration of approximately $1 \times 10^6$ cells per ml were cultured in 50 ml volumes in RPMI-1640 medium supplemented with 10% (v/v), 2 mM glutamine, 100 U/ml penicillin, 100 micrograms per milliliter ("μg/ml") streptomycin, and 2.5 μg/ml Con A. The cells were cultured for approximately 16 hours in a humidified atmosphere of 5% $CO_2$ in air. After this period of time, viable cells were harvested by centrifugation.

Total RNA was extracted from the mononuclear cells generally by the method as described by Chirgwin et al., supra. In this procedure guanidinium thiocyanate was used to denature the cellular protein including the RNase at a rate that exceeds the rate of RNA hydrolysis by RNase. The mRNA was removed from the cellular protein by ethanol precipitation followed by resuspension (extraction) with 8M guanidine HCl, 25 mM sodium acetate. Guanidine HCl extracted RNA was the reextracted with an equal volume of phenol/chloroform: isoamyl alcohol (25 volumes/24 volumes: 1 volume). The aqueous phase containing the RNA resulting from such extraction process was then rendered 50 mM sodium acetate, and precipitated by addition of 0.6 volume ethanol. RNA was collected by freezing at $-20°$ C. followed by centrifugation.

Thereafter, polyadenylated mRNA was separated from the extracted protein on an oligo (dT)-cellulose chromatography column using the method disclosed by Maniatis et al., supra at 197. Briefly, the column was prepared with application buffer composed of 20 mM Tris-Cl (pH 7.6), 0.5M NaCl, 1 mM ethylene diamine tetraacetate ("EDTA") and 0.1% sodium dodecyl sulfate ("SDS"). The protein pellet was dissolved on water and application buffer and then loaded onto the column. The nonadsorbed material was eluted by initial washings with application buffer followed by additional washings with application buffer containing 0.1M NaCl. The retained polyadenylated mRNA was eluted with buffers of reduced ionic strength composed of 10 mM Tris-Cl (pH 7.5), 1 mM EDTA and 0.05% SDS. The eluted polyadenylated mRNA was precipitated at $-20°$ C. with 1/10 volume sodium acetate (3M, pH 5.2) and 2.2 volumes of ethanol. After elution of the polyadenylated mRNA from the oligo (dT)-cellulose column, the integrity of the polyadenylated mRNA was confirmed by electrophoresis through agarose gels as detailed in Maniatis et al., supra at 199.

EXAMPLE 2

Construction of cDNA Library

A library of double-stranded cDNA corresponding to the mRNA was prepared from the purified mRNA in Example 1 by employing the standard procedure detailed by Maniatis et al., supra at 229 as modified by Gubler and Hoffman, supra. Oligo-dT was hybridized to the polyadenylated tail of the mRNA to serve as the primer for the reverse transcription of the first cDNA strand. The enzyme avian myeloblastosis virus ("AMV") reverse transcriptase synthesized the first cDNA strand by using the mRNA as a template. Briefly, the synthesis of the first cDNA strand is carried out in a reaction volume of 20–40 μl containing 50 mM Tris.HCl [pH 8.3], 10 mM $MgCl_2$, 10 mM dithiothreitol, ("DTT"), 4 mM Na.pyrophosphate, 1.25 mM dGTP, 1.25 mM dATP, 1.25 mM TTP, 0.5 mM dCTP, 15–20 μCi of [α−$^{32}$P] dCTP [3,000 Ci/mmol], 100 μg/ml of oligo (dT$_{12-18}$), 150 μg/ml mRNA (from Example 1), 3000 units AMV reverse transcriptase/ml. The reaction was carried out at 43° C. for thirty minutes and then stopped by adding EDTA to 20 mM. The reaction products were extracted with phenol and precipitated with ethanol out of 2M $NH_4$.acetate, as described by Okayama and Berg, *Mol. Cell. Biol.*, 2:161-170 (1982). The second cDNA strand was synthesized in a reaction containing 100 μl of 20 mM Tris HCl as above [pH 7.5], 5 mM MgCl, 10 mM $(NH_4)_2SO_4$, 100 mM KCl, 0.15 mM β-NAD, 50 μg/ml BSA, 40 μm dNTPs, 8.5 units/ml of *E. coli* RNase H, 230 units/ml DNA polymerase I, 10 units/ml *E. coli* DNA ligase. This mixture is incubated at one hour for 12° C. and then for a further hour at 22° C. Thereafter, EDTA is added to 20 mM to stop the reaction. The resulting double-stranded cDNA is extracted with phenol as described above.

The double-stranded cDNA was fractionated into size classes by Sephacryl S-400 (Pharmacia Fine Chemicals) column chromatography and monitored by analysis using alkaline agarose electrophoresis employing end-labeled fragments of pBR332 DNA as molecular-weight markers. DNA strands having a length of less than 500 bp were culled out to avoid needless cloning of these undersized cDNA fractions.

The double-stranded cDNA fractions, as prepared above, were inserted into the Pst I site of the pBR322 plasmid (Pharmacia Fine Chemicals) the method disclosed by Maniatis et al., supra, beginning at 239. In this procedure the double-stranded cDNA was tailed with poly (dC) at its 3' ends. The plasmid pBR322 was digested with Pst I endonuclease and then tailed with poly (dG) at its 3' ends. The tailed plasmid DNA and the tailed cDNA were annealed with annealing buffer (0.1M NaCl, 10 mM Tris-Cl (pH 7.8) and 10 mM EDTA) to form novel recombinant plasmids. All restriction enzymes described herein are commercially available from New England Biolabs, Beverly, MA.

The recombinant plasmids were transformed into $E.$ $coli$ strain MM294 by using the procedure of Hanahan, supra in which the $E.$ $coli$ cells were prepared by growth in elevated levels of $Mg^{2+}$. The transformation hosts were plated and then transformants were identified by use of tetracycline as a phenotypic identifier. By use of this technique, applicants obtained approximately 35,000 independent transformants.

EXAMPLE 3

Preparation of Human IL-2 cDNA Screening Probe

Total RNA was extracted from Jurkat cells and polyadenlylated mRNA was separated therefrom on an oligo (dT)-cellulose chromatography column, using the protocols set forth in Example 1. The Jurket cell line is available from the ATCC (Accession No. ATCC-CRL-8163). The integrity of the resulting polyadenylated mRNA was confirmed by agarose gel electrophoresis. A library of double-stranded cDNA corresponding to the human mRNA was prepared by the method set forth above in Example 2. The resulting double-stranded cDNA fractions of sizes greater than 500 bp were inserted into the Pst I site of the pBR322 plasmid by the homopolymeric tailing method set forth in Example 2. The recombinant plasmids were transformed into $E.$ $coli$ strain MM294 and then the transformants were identified by use of tetracycline as a phenotypic identifier. By this process, applicants identified approximately $1 \times 10^6$ independent transformants.

A synthetic oligonucleotide probe was chemically synthesized by standard triester method, as detailed by Sood et al., supra, and Hirose et al., supra, and then radiolabeled with $^{32}P$ for use in screening the murine cDNA library. The probe was composed of the following nucleotide sequence: 5'-AA TGT GAG CAT CCT GGT GAG-3', which corresponds with nucleotides 173 through 192 in FIG. 1. To facilitate labeling, the 5' ends of the oligonucleotides are synthesized with OH termini, thereby eliminating the phosphatase treatment which typically must be employed when labeling DNA fragments. The labeling protocol included dding 1 $\mu$l of the synthetic oligonucleotides to 16 $\mu$l of $^{32}P$-ATP (7000 Ci/mM), 1 $\mu$l (10 U) of T4 polynucleotide kinase and 2 $\mu$l of 10×kinase buffer I (0.5M Tris-Cl (pH 7.6), 0.1 $MgCl_2$, 50 mM dithiothreitol, 1 mM spermidine and 1 mM EDTA). The reaction was carried out at 37° C. for thirty minutes, and thereafter the synthesized oligonucleotides were extracted with phenol/choroform. The labeled probes were separated from unlabeled oligonucleotides by chromatography on or centrifugation through Sephadex G-50 columns (Pharmacia Fine Chemicals).

To facilitate initial screening of the human cDNA library, the transformed bacterial cultures were grouped into pools, each having approximately 5,000 different clones. Plasmid DNA was removed from samples of the host bacteria by standard alkaline lysis method detailed by Ish-Horowicz and Burke, $Nucl.$ $Acids$ $Res.,$ 9:2989 (1981). The isolated plasmids were digested to completion with Pvu II and Hind III standard procedures. Next the plasmid digests were fractionated by electrophoresis through 0.8% agarose gel and then blotted onto nitrocellulose filter by the standard method of Southern, supra. The DNA that bound to the nitrocellulose filter was hybridized with the labeled synthetic oligonucleotide probe using the procedure detailed in Example 4, infra. The putative pool(s) of clones from which hybridizing bands of DNA were obtained was screened by direct colony hybridization with the radiolabeled synthetic probe, and a single positive colony was identified.

Plasmid DNA was prepared from the identified positive colony by the procedures set forth above and then sequenced as discussed in Example 5, infra. The nucleotide seqence of the isolated human plasmid DNA fragment, as shown in FIG. 1, was found to include substantially the entire nucleotide sequence of the open reading frame of human IL-2 gene.

The 708 bp fragment of the human IL-2 cDNA clone defined by the solid underline in FIG. 1 (nucleotide No. 12 to nucleotide No. 719 inclusive) was selected as a probe for screening the human plasmid DNA prepared in Example 2 above. The probe fragment was removed from the human cDNA clone by double digestion with the restriction enzymes Pst I and Rsa I followed by agarose gel electrophoresis.

The cDNA nucleotide probe was radiolabeled by nick translation by the standard procedure set forth in Maniatis et al., supra at 108, and discussed above. By this procedure, the probe was labeled to a specific activity of approximately $5 \times 10^8$ CPM/$\mu$g DNA. Prior to use in screening protocols, the label probe was denatured by boiling in water at 100° C. for ten minutes followed by chilling on ice.

EXAMPLE 4

Screening of cDNA Library

To facilitate initial screening of the cDNA library prepared in Example 2 above, the transformed bacteria cultures were grouped into pools each having approximately 2,500 different clones. Plasmid DNA was removed from samples of the host bacteria by standard alkaline lysis method detailed by Ish-Horowicz and Burke, supra. The isolated plasmids were cleaved with Pst I and then fractionated by electrophoresis through 1.0% agarose gel with markers of appropriate size. The agarose gel was blotted onto nitrocellulose filter using the method described by Southern, supra. After the transfer process, the filter was air-dried and baked for two hours at approximately 80° C. under a vacuum to bind the DNA fragments to the nitrocellulose.

The bound DNA was next hybridized with the labeled cDNA probe. Briefly, the baked nitrocellulose was incubated at 55° C. for 2-4 hours in prehybridization buffer composed of 6×SSC, 0.5% NP40 detergent, 0.1% sarcosyl, 5×Denhardt's solution (0.02% Ficoll, 0.02% polyvinyl pyrrolidone, 0.02% BSA) and 100 μg/ml denatured salmon sperm DNA (Sigma Type III, sodium salt). The filter was then incubated overnight at 55° C. with the $^{32}$P-labeled cDNA probe (10$^6$ cpm/ml) (from Example 3) in hybridizing solution as above. After overnight hybridization, the filter was washed extensively with 6×SSC at room temperature and then for 1 hour at 42° C. and then for 1.5 hours at 55° C. with 6×SSC. After air drying, the filter was subjected to autoradiography at −70° C.

From the autoradiography, applicants found a number of strongly hybridizing bands. One putative pool of clones from which the plasmid DNA that produced a strongly hybridizing band was obtained was subdivided into pools of approximately 500 transformants and the hybridization screening procedure repeated. The putative subpool from which a strongly hybridizing band of DNA was seen was then plated. The resulting colonies were probed with the radiolabeled nucleotide probe by the well-known methods of Grunstein and Hogness, supra, using the hybridizing conditions described above. By this process, a single positive host colony was identified.

EXAMPLE 5

Characterization of Screened cDNA

Plasmid, designated as bIL-2-4, was prepared with cDNA from the identified positive colony by the procedures set forth in Example 4. Samples of the host plasmid transformed into *E. coli* are on deposit with the ATCC under Accession No 53184. The cDNA inserts prepared from the plasmid DNA removed from the positive host colony was sequenced by standard chain-termination protocol essentially as described in the Amersham Handbook, supra, with the variations set forth below. The cDNA insert was digested with Pst I and/or Rsa I and then subcloned into strains mp18 and mp19 of the M13 single-stranded filamentous phage vector (Amersham, Arlington Heights, IL). The mp18 and mp19 phage vectors, as set forth in Vorrander et al., supra, contain the following unique cloning sites: Hind III; Sph I; Pst I; Sal I; Acc I; Hinc II; Xba I; BamHI; Xma I; Sma I; Kpn I; Sst I; and, EcoRI. The composition of the mp18 and mp19 vectors are identical, with the exception that the order of the above-identified restriction sites are reversed in the mp19 vector so that both strands of the cDNA insert may be conveniently sequenced with the two vectors. The mp18 and mp19 vectors, with a corresponding strand of the cDNA inserted therein, were used to transform *E. coli* JM107 of the strain K12 (Bethesda Research Laboratories, Bethesda, MD) to produce replicate single-stranded DNA templates containing single-stranded inserts of the sense and antisense strands.

The synthetic universal primer: 5'-CCCAGTCAC-GACGTT-3' (P-L Biochemicals, Milwaukee, WI), was annealed to the single-strand DNA templates and used to prime DNA synthesis as described above at page 10. Thereafter, the extension fragments were size-separated by gel electrophoresis and autoradiographed from which the nucleotide sequences of the fragments were deduced.

Deoxyadenosine 5' (α−[$^{35}$S] thio) triphosphate (hereinafter "dATP [α−$^{35}$S]") was used as the radioactive label in the dideoxy sequencing reactions. Also, rather than using the gel set forth at page 36 of the Amersham Handbook, a 6% polyacrylamide gel was employed (6% polyacrylmide gel, 0.4 mm thick, containing 7M urea, 100 mM Tris borate [pH 8.1], and 2 mM EDTA).

As noted above, the nucleotide sequence of the bIL-2-4 cDNA is illustrated in FIG. 2. The coding region of the bIL-2 gene extends from nucleotide No. 18 (Met residue) to nucleotide No. 482 (Thr residue), and the mature protein begins at the amino acid residue (Ala) corresponding to nucleotide No. 78. The corresponding amino acids, as determined by the nucleotide sequence, are set forth below the codons.

EXAMPLE 6

Expression of Mature bIL-2 in Yeast Hosts

The coding region and a portion of the 3' flanking region of the bIL-2 gene was removed from the bIL-2-4 cDNA clone of FIG. 2 and inserted into plasmid, pα3 with a linking oligonucleotide to form a recombinant expression plasmid, designated as pYαfBoIL-2, to direct high level bIL-2 expression in yeast host cells. The starting plasmid pα3 is on deposit with the ATCC under Accession No. 53220. As shown in FIG. 3, pα3 includes an origin of replication and an Amp$^r$ resistant gene from plasmid pBR332 (thick line portion). The pYαfGM-2 plasmid also includes the 2u circle origin of replication and a Trp I gene for selection of transformed yeast hosts (Trp-auxotrophs), (thin line portion in FIG. 3). The starting plasmid further includes the yeast α-factor promoter and leader sequences and initiation codon ATG for use in directing high level transcription and secretion of bIL-2 (stippled box portion in FIG. 3). The bIL-2 sequences (hatched box portion in FIG. 3) are fused to the downstream (3') end of the α-factor sequences through the use of a synthetic oligonucleotide, as discussed more fully below.

The pα3 plasmid also includes, as shown in FIG. 3, a linking oligonuleotide (shown in solid box portion) having cohesive Kpn I 5' and 3' ends and various restriction enzyme cleaving sites, including Pst I, Avr II and Nco I sites, for convenient ligation to desired cDNA cloning fragments. To prepare the pYαf BoIL-2 plasmid, the pα3 plasmid was initially digested with the restriction enzymes Kpn I and Nco I in a standard protocol, for instance, as set forth in Maniatis et al., supra. The resulting major fragment was isolated by electrophoresis through agarose gel using the method detailed in Maniatis et al., supra at 199. By this digestion procedure, most of the multiple cloning sites of the linking oligonucleotide shown in FIG. 3 are removed from the major fragment.

The coding region and a portion of the 3' flanking region of the bIL-2 gene, from the Hgi AI (nucleotide No. 77) to the Ssp I restriction enzyme site (nucleotide No. 535) was removed from the bIL-2-4 clone by use of Hgi AI and Ssp I restriction enzymes in standard protocol, for instance as set forth in Maniatis et al., supra. The resulting minor fragment was treated with T4 DNA polymerase to remove the 3' overhang at the 5' Hgi AI terminal. Nco I linkers were added to the 3' end of the isolated cDNA to enable the cDNA fragment to be ligated into the Nco I site of the pα3 vector. The Nco I linkers, of the composition: GGGCCATGGCCC, were added to the 3' end of the cDNA by standard procedure, for instance as set forth in Maniatis et al., supra. Thereafter, the Nco I linkers were digested with Nco I restriction enzyme to generate a cohesive 3' end. The resulting 455 base pair bp Hgi AI-Nco I bIL-2 fragment was purified by electrophoresis through agarose gel.

Next, a linking oligonucleotide was prepared for linking the 5' terminal of the bIL-2 cDNA fragment, as prepared above, to the pα3 cloning vector. The composition of the oligonucleotide, as shown in TABLE 2 below, and in FIG. 3, includes the Kpn I cohesive 5' terminal followed by an α-factor processing region (AAA-AGN). The codon GCA encoding Ala, is located 3' to the α-factor processing site to serve as the first codon of the mature bIL-2 gene. This first codon was lost from the bIL-2 cDNA by digestion with Hgi AI and subsequent removal of the 3' overhang thereof.

TABLE II

| 5'CT | TTG | GAT | AAA | AGA | GCA3' |
|---|---|---|---|---|---|
| 3'CAT | GGA | AAC | CTA | TTT | TCT | CGT5' |

To form the pYαF BoIL-2 plasmid, a three-way ligation is performed with the Kpn I-Nco I digested pα3 plasmid, the Kpn I-blunt linking oligonucleotide (TABLE 2), and the blunt-Nco I bIL-2-4 cDNA fragment.

It is to be understood that other standard recombinant DNA techniques could be used to generate the same expression vector, and that the construction detailed above is an illustrative but nonlimiting example of various strategies that could be used to prepare a bIL-2 cDNA fragment for insertion into the pYαfBoIL-2 vector. In addition, the bIL-2-4 cDNA fragment could be inserted into other appropriate vectors for successful high level expression of bIL-2 in yeast hosts.

The pYαfBoIL-2 expression plasmid was transformed into yeast strain 79 (α, Trp 1-1, Leu 2-1) of S. cerevisiae for selection of Trp+ transformants by standard techniques. Prior to transformation, the strain 79 was grown in culture in YEPD medium (1% [wt/vol] yeast extract, 2% [wt/vol] peptone, 2% [wt/vol] glucose), to a density of $2 \times 10^7$ cells/ml. Cells were harvested by centrifugation at $1000 \times g$ for 5 minutes at 22° C., and then the resulting pellet was washed with sterile, distilled water.

The yeast cells were then concentrated by resuspending in 1/10 vol. of SED (1M sorbitol, 25 mM EDTA [pH 8.0], and 50 mM dithiothreitol) and incubating for 10 minutes at 30° C. The cell-buffer mixture was then centrifuged for 5 minutes at $300 \times g$. The pellet was washed once with 1/10 vol. of 1M sorbitol and the cells resuspended in 1/10 volume of SCE (1M sorbitol, 0.1M sodium citrate [pH 5.8], 0.01M EDTA). Glusulase, to break down the cell walls, in an amount of $10^{-3}$ vol., was added to the solution and then the solution incubated at 30° C. for 30 minutes with occasional gentle shaking. The presence of sheroplasts was assayed by diluting 10 microliters of the yeast cells into a drop of 5% SDS (wt/vol) on a microscope slide to observe for "ghosts" at $400 \times$ phase contrast. The cell mixture was then centrifuged at $300 \times g$ for 3 minutes. The resulting pellet was twice washed with 1/10 vol. of 1M sorbitol. The pellet was then once washed in CaS (1M sorbitol, 10 mM CaCl₂).

The yeast spheroplasts were then transformed with the previously prepared expression vector in a procedure adapted from Beggs, supra. The pelleted spheroplasts were suspended in 1/200 vol. of CaS and then divided into 100 microliter aliquotes in 1.5 ml Eppendorf tubes. Then, from 1 to 10 μl of the plasmid DNA were added to each aliquot (0.5 to 5 μg). The mixture was incubated at room temperature for 15 minutes and then 1 ml of PEG (20% PEG 4000, 10 mM CaCl₂, 10 mM Tris-HCl [pH 7.4]) was added to each aliquot to promote DNA uptake. After 15 minutes at room temperature, the mixture was centrifuged for 5 minutes at $350 \times g$. The resulting pellet was resuspended in 150 μl of SOS (10 ml of 2M sorbitol, 6.7 ml of YEPD medium, 0.13 ml of 1M CaCl₂, 27 μl of 1% tryptophan and 3.7 ml of water). This mixture was incubated for 20 minutes at 30° C. The cells were then plated.

Prior to plating the protoplast/DNA mixture, selective plates were preincubated at 37° C. Three ml of melted top agar (45° C.), composed of 18.2 ml of sorbitol, 2 gm agar, 0.6 gm Difco yeast nitrogen base (without amino acids), 2 gm glucose, 0.1 ml of 1% adenine, 0.4 ml of 1% uracil and amino acids as required, was then added to each aliquot of transformed cells and the tube contents poured on the selective plates. The plates were incubated from 2 to 4 days at 30° C. Colonies which developed in the Trp minus medium contained plasmids that have the Trp 1 gene, i.e., those that are transformed.

Prior to biological assay, the transformants were grown in 20–50 ml of YEPD at 30° C. to stationary phase. At the time of harvest, the protease inhibitors phenylmethylsulfonyl fluoride (PMSF) and Pepstatin A were added to a final concentration of 1 mM and 10 μM, respectively. The cells were then removed by centrifugation at $400 \times g$ and the medium was filtered through a 0.45 micron cellulose acetate filter (Corning Glass Works, Corning, NY). The sterile supernates were stored at 4° C. The resulting supernates, as assayed with the target IL-2 dependent bovine cell, exhibited bIL-2 activity of approximately $1.3 \times 10^6$ units per milliliter.

EXAMPLE 7

Expression of bIL-2 in Bacteria Host

Figure 4A:
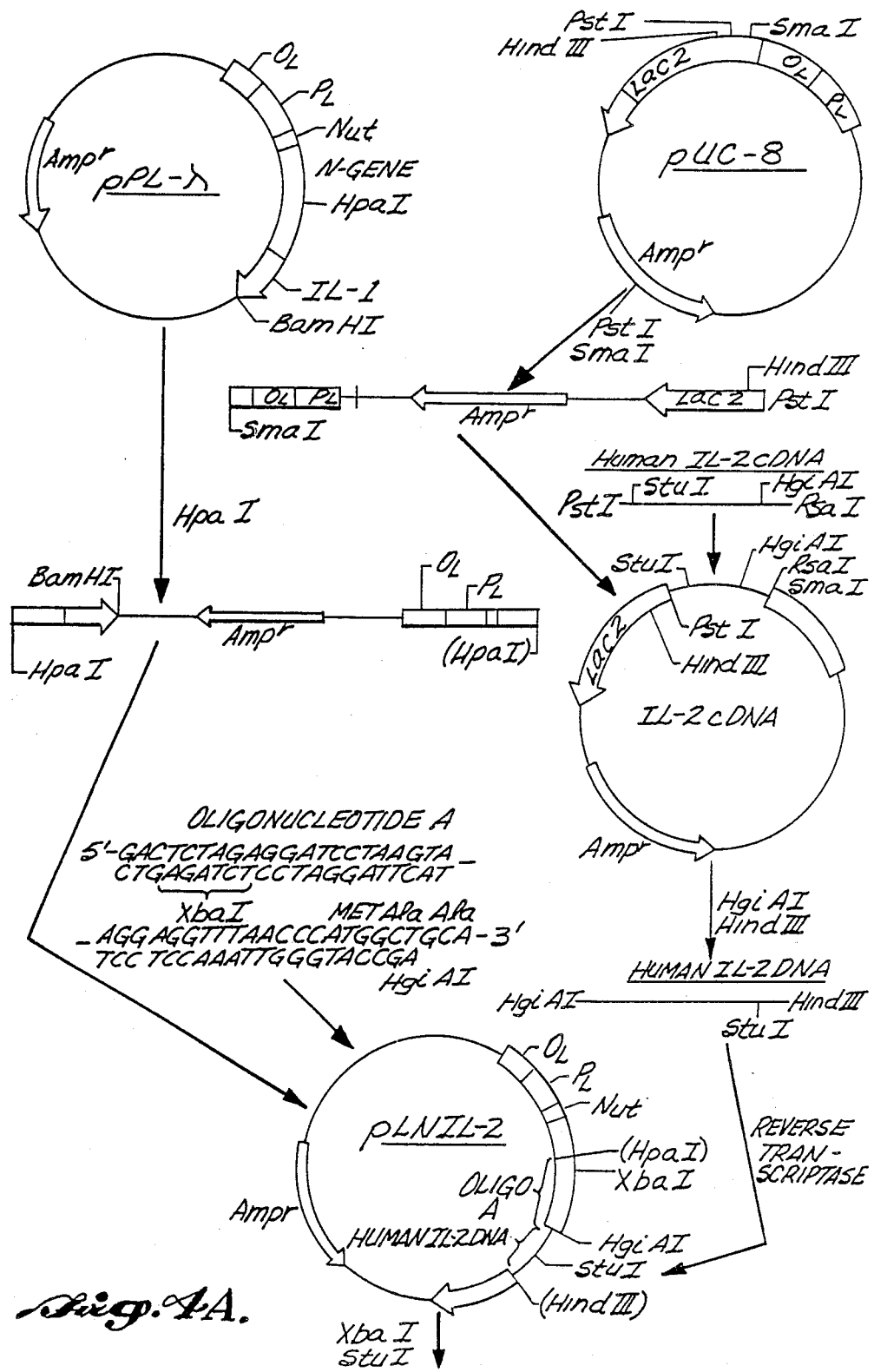
FIGS. 4A and 4B (hereinafter jointly referred to as "FIG. 4") illustrate the pLN bov IL-2 plasmid, with the coding region of the bIL-2 gene inserted therein, for use in transforming bacterial host cells to express functional bIL-2.
Figure 4B:
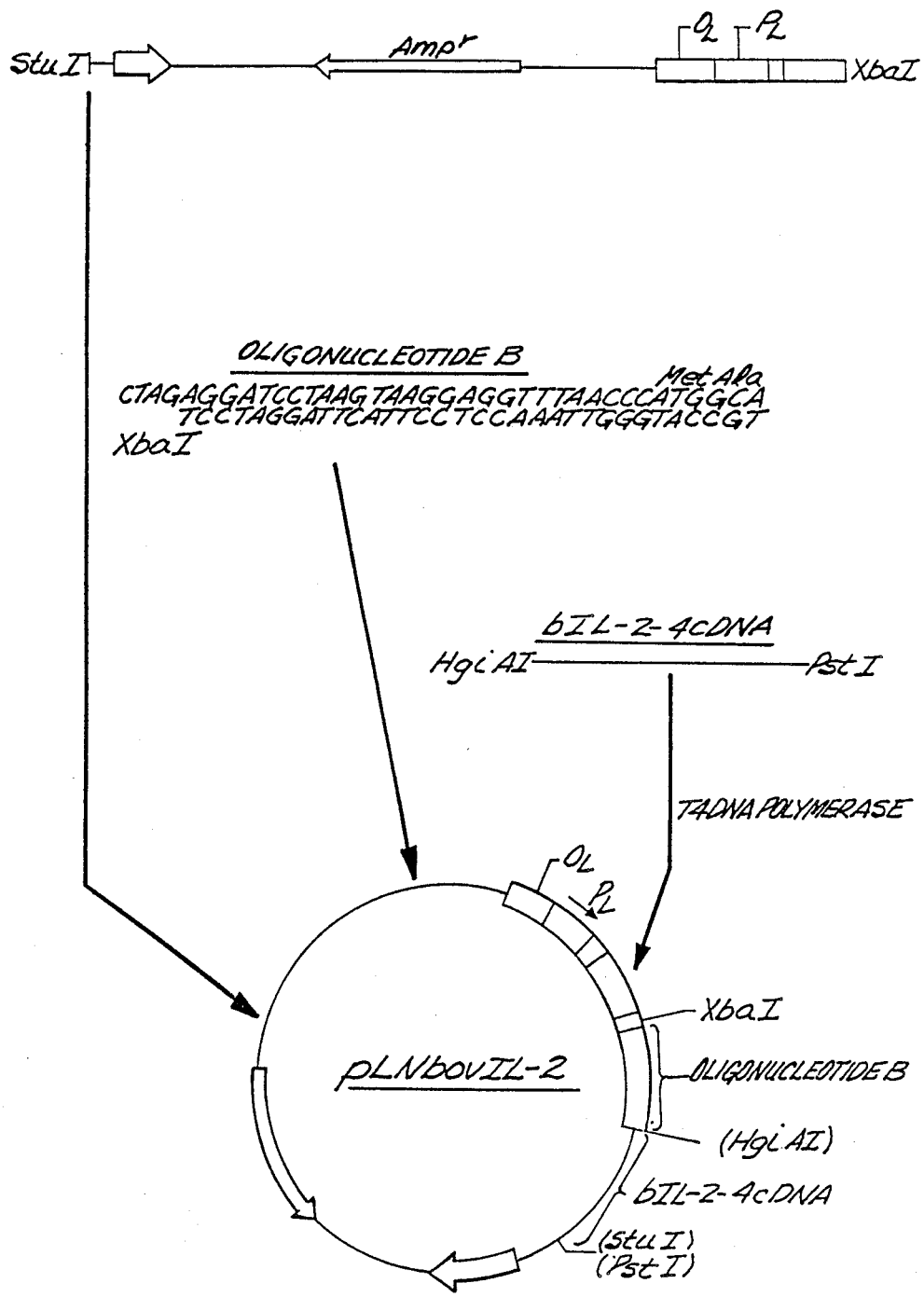

The coding region of the bIL-2 gene shown in FIG. 2 extending from the Hgi AI (nucleotide No. 77) to the Pst I restriction site (nucleotide No. 533) in the 3' flanking region of the gene was inserted into an expression vector to direct bIL-2 expression in E. coli. This expression vector, designated as pLN bov IL-2 and illustrated in FIG. 4, was constructed from base plasmid pPL-λ (Pharmacia Fine Chemicals, Piscataway, NJ, Cat. No. 27-4946-01). The genome of plasmid pPL-λ plasmid contains a phage $P_L$ promoter and an N gene. As illustrated in FIG. 4, the pPL-λ plasmid contains an origin of replication (from plasmid pBR332) for high copy DNA replication in E. coli and an ampicillin resistant gene, also from plasmid pBR332, for selection of transformed E. coli hosts. The pLN bov IL-2 plasmid has been deposited with the ATCC under Accession No. 53232.

The pLN bov IL-2 plasmid was constructed in two stages. As shown in FIG. 4, the first stage included the pPL-λ plasmid, which was digested with the restriction enzyme HpaI, the synthetic oligonucleotide A, and an insert DNA fragment which contained a portion of the human IL-2 cDNA gene.

The cDNA encoding the human IL-2 gene was removed from the human cDNA clone by double digestion with the restriction enzymes Pst I and Rsa I, as described above in Example 3. This DNA fragment was then ligated into the cloning vector pUC-8 (Pharmacia Fine Chemicals) Cat. No. 27-4916-01) which had been digested with the restriction enzymes Sma I and Pst I. Digestion of the resultant plasmid with Hgi AI and Hind III allowed isolation of a DNA fragment containing a portion of the human IL-2 cDNA gene extending from the Hgi AI, site at nucleotide No. 66 in FIG. 1. to the Hind III site in pUC-8 which is 4 nucleotides beyond the Pst I site. Before subsequent ligation, the 5' overhang at the 3' end of the IL-2 gene was filed in the use of reverse transcriptase.

The pPL-λ plasmid, cut with Hpa I, was ligated with the oligonucleotide A, which had a blunt 5' end and a Hgi AI-compatible 3' end, and with the above-described human IL-2 cDNA fragment which had a Hgi AI 5' end and a blunted Hind III end. Ligation was performed with the plasmid DNA at 4 μg/ml and at molar ratios of vector to insert DNA to oligonucleotide of 1 to 20 to 8 as described by Maniatis et al., supra. The resulting recombinant plasmid, designated as pLNIL-2, was then transformed into *E. coli* strain (ATCC No. 31343) containing the plasmid pRK248cIts (ATCC No. 33766), which has a gene encoding a thermolabile *E. coli* cI repressor of the $P_L$ promoter. In the transformation procedure, the entire ligation mix was added to competent *E. coli* RR1 (pRK248cIts). The mixture was allowed to set an ice for 30 minutes and then was pulsed with heat to 30° C. for 4 minutes and grown for 1 hour in L-broth at 30° C. Transformed hosts were then plated on L plates containing tetracycline and ampicillin, 17 μg/ml.

The plasmid pLNIL-2 was then used in the second stage to produce the plasmid pLN bov IL-2 as shown in FIG. 4. The coding sequence for human IL-2 and a portion of the oligonucleotide A were removed from pLN-IL-2 by digestion with Xba I and Stu I. (The Stu I site is at position No. 500 in FIG. 1). Insert DNA containing the coding region for bIL-2 was isolated from the plasmid bIL-2-4 by digestion with the restriction enzymes Hgi I and Pst I. The 3' overhangs at both ends of the isolated DNA fragment were blunted by digestion with T4 DNA polymerase. Ligation of the pLN IL-2 vector, digested with Xba I and Stu I, the bIL-2 insert DNA, and oligonucleotide B in FIG. 4 at the relative concentrations described for ligation in stage 1 above resulted in production of the plasmid pLN bov IL-2. The resulting recombinant plasmid pLN bov IL-2 was then transformed into *E. coli* strain RR1 (pRK248cIts) by the procedure described above.

As illustrated in FIG. 4 and discussed above, the synthetic oligonuceotide B was employed for efficient translation initiation of the bIL-2 gene. The composition of the oligonucleotide B includes an Xba I cohesive 5' terminus for ligation to the Xba I end of the cut pLN IL-2 vector and a blunt 3' terminus for ligation to the 5' terminus of the bIL-2 DNA fragment. An ATG initiation codon and the nucleotides GCA encoding the N-terminal alanine of the bIL-2 gene are located at the 3' end of the oligonucleotide. As discussed above, the intermediate sequences of the oligonucleotide compose the translation initiation sequences. The oligonucleotide was chemically synthesized by the triester technique as detailed by Sood et al., supra and Hirose et al., supra; however, it is to be understood that the oligonucleotide can be prepared by other methods, such as by the phosphodiester method.

Unless otherwise indicated, all digestions with restriction enzymes, ligations, isolations of DNA fragments by agarose gel eletrophoresis, digestions of single-stranded DNA ends with T4 DNA polymerase, and fill-in reactions with reverse transcriptase were performed as described in Maniatis et al., supra.

Cultures containing pLN bov IL-2 in *E. coli* strain RR1 (pRK248cIts) were grown in S.I. medium [M-9 medium (Maniatis et al., supra) supplemented with 32 g/l tryptone and 20 g/l yeast extract] containing tetracycline and ampicillin at 17 μg/ml overnight at 30° C. They were then diluted 100-fold into S.I. medium without ampicillin and grown to an absorbance at 600 nm of 0.5 and shifted to 42° C. for 4 hours to promote depression. One ml samples of the culture were pelleted by centrifugation at 4° C. and frozen by exposure to a mixture of dry ice and methanol. The pellets were then resuspended in 150 μl of 7M guanidine hydrochloride and refrozen on dry ice/methanol. The existence of biological activity in the guanidine extract was then ascertained by the bIL-2 assay discussed supra. Applicants found that the pLN bov IL-2 plasmid expressed biological activity of over $10.2 \times 10^6$ units/ml. This confirms that the cDNA characterized in FIG. 2 corresponds to the bIL-2 gene.

EXAMPLE 8

Purification of rbIL-2.

The rbIL-2 from the yeast extract or the guanidine extract, for instance form Examples 6 and 7 above, was purified to homogeneity by HPLC processes using a Waters LC500A preparative HPLC chromagraph equipped with a Waters Preparative Gradient Generator with optical absorbance at 280 nm being monitored with an LKB 2238 Uvicord II absorbance detector (LKB Instruments, Inc.). Medium containing expressed rbIL-2 was pumped directly onto a Waters PrePAK column (Waters Associates), at a flow rate of about 100 ml/min. The column was packed with Vydac C-4 resin, 15-20 micron particle size. The column previously had been equilibrated with 0.1% TFA (v/v). Approximately seven liters of medium were applied to the column at one time. The loaded column was flushed with 0.1% TFA in $H_2O$ (v/v) to remove non-bound components until the absorbance at 280 nm returned to baseline (preloading) values by use of the LKB 2238 Uvicord II detector. Elution of the bound proteins was accomplished with a linear gradient of 0–100% acetonitrile in 0.1% TFA (v/v) at a 2% per minute gradient at a flow rate of approximately 100 ml/min.

Figure 5A:
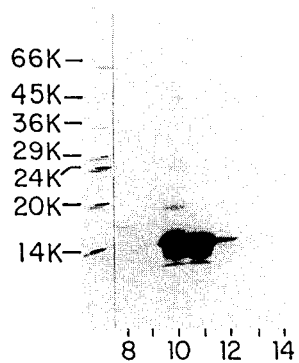
FIGS. 5A and 5B illustrates the partial purification of recombinant bovine rbIL-2 by HPLC, with FIG. 5A illustrating the results of polyacrylamide gel electrophoresis of active fractions recovered from the initial HPLC column. The numbers below the lanes correspond to fractions eluted from the first HPLC column with molecular weight markers indicated along the first (left-hand side) column.
Figure 5B:
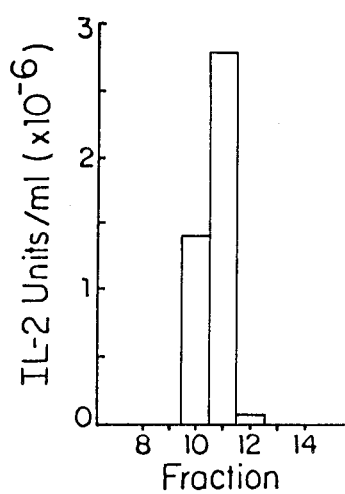

One minute fractions were collected and analyzed using the IL-2 dependent bovine cell line assay detailed above. As shown in FIG. 5, significant activity was found in fractions 10 and 11. Polyacrylamide gel electrophoresis of these fractions showed that although significant concentration of the rbIL-2 was achieved in first HPLC procedure, the protein was not purified to homogeneity.

Fractions containing bIL-2 activity obtained from the first HPLC process, fraction numbers 10 and 11, were pooled and diluted 1:2 with buffer A (0.9M acidic acid, 0.2M pyridine, pH 4.0) and reapplied at a rate of 50 ml/min. to the same PrePAK column used above, which had been previously equilibrated with buffer A and 20% buffer B (60% n-propanol in 0.9M acidic acid, 0.2M pyridine, pH 4.0). After loading, the column was initially washed with buffer A to remove non-bound components. Then the protein was eluted from the column with a 20-80% gradient of buffer B applied to the column at a 1% per minute gradient and a flow rate of about 15 ml/min.

Figure 6A:
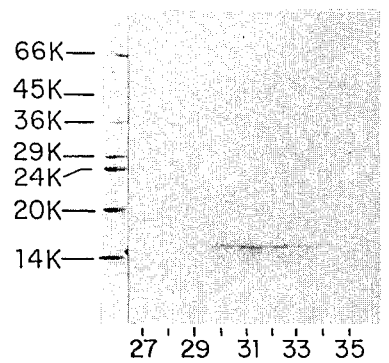
FIGS. 6A and 6B illustrate the purification of the rbIL-2 to homogeneity by a second HPLC treatment.
Figure 6B:
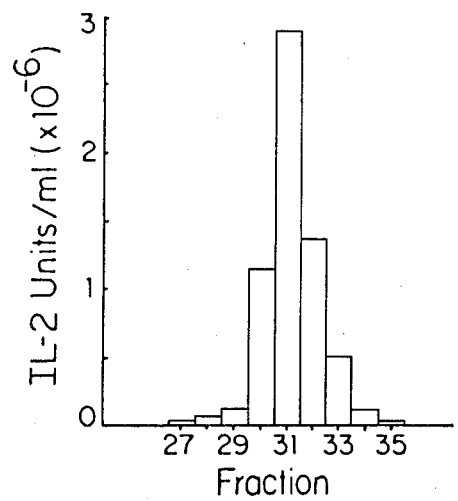

One minute fractions were collected form the second HPLC procedure and analyzed by use of the biological assay set forth above, by polyacrylamide gel electrophoresis and by fluorescamines, Undenfriend et al., *Science*, 178:871 (1972). From this analysis, as illustrated in FIG. 6, homogeneous rbIL-2 was found predominantly in fraction numbers 30-32. Also, the rbIL-2 was determined to have a molecular weight of approximately 16,000 daltons and was the only protein product detected in the fractions containing bIL-2 activity. Recovery of the activity in fractions 30-32 was approximately 86% of that applied to the second HPLC column.

Natural bIL-2 has been reported to have a molecular weight of about 20,000-23,000 daltons. Brown et al., *J. Immunol*, 133:3184 (1985). From the cDNA encoding bIL-2 discussed above and set forth in FIG. 2, the predicted molecular weight of the molecule is approximately 15,450 daltons which is in conformity to that determined for rbIL-2 by the polyacrylamide gel electrophoresis analysis. A difference in molecular weight between the natural and recombinant forms of bIL-2 may be due to a potential N-linked glycosylation site at the Asn residue at position number 70 in FIG. 2. From the foregoing, it would appear that rbIL-2 does not require glycosylation in order to induce poliferation of responsive T cells.

The homogeneous rbIL-2 was analyzed for amino acid composition. Samples of the purified product were hydrolyzed in vacuo with constant boiling in HCl (redistilled from concentrated HCl; Kodak, Rochester, NY) for 24 hours. After hydrolysis, the samples were evaporated to dryness under vacuum and resuspended in 0.2N sodium citrate, pH 2.2. Samples were injected into a single-column amino acid analyzer (Model 4150-alpha; LKB Instruments, Inc.), with the amino acid residues being detected by standard ninhydrin testing. The areas of the output "peaks" corresponding to the quantities of particular amino acids present were integrated with an LKB Model 2220 recording integrator. The results of the amino acid composition analysis was consistant with that predicted from the bovine cDNA detailed above.

The homogeneous protein from the second HPLC procedure was also sequenced by standard methods. Samples of the rbIL-2 were dried, vacuumed to a small volume and then subjected to an automated amino terminal Edman degration using an Applied Biosystems Model 740 A sequencer (Foster City, CA) using the reagents and program supplied by the manufacturer. From these procedures, the first 20 residues of the amino terminal portion of the rbIL-2 was found to be of the same sequence as that predicted from the cDNA as set forth in amino acid residue numbers 21-41 in FIG. 2. In the protein sequencing procedure, phenylthiohydantoin amino acids were identified by reverse phase HPLC on either a DuPont Zorback ODS 4.6 mm×30 cm column or an IBM-cyano 4.5 mm×25 cm column.

EXAMPLE 9

Analysis of mRNA

The expression of bIL-2 mRNA isolated from bovine lymph node cells was analyzed by Northern blot by hybridization with a probe derived from the bIL-2 cDNA. In this regard, total RNA for Northern blots was isolated by the guanidium thiocyanate method set forth supra in Example 1 from Con A stimulated and unstimulated bovine lymph node cells. The RNA samples were sized by electrophoresis in 1.1% agarose gels containing formaldehyde to denature the RNA so that the rate of migration of the RNA through the gel was proportional to its molecular weight. A standard protocol for electrophoresis of the RNA through agarose gels containing formaldehyde is set forth in Maniatis et al., supra at 202.

After electrophoresis the formaldehyde-denatured RNA was transferred to nylon membranes (Hybond-N, Amersham) using a standard protocol, for instance, as detailed in Maniatis et al., supra at 203, for subsequent hybridization with $^{32}$P-labeled RNA probe transcribed in vitro by SP6 RNA polymerase by the procedure set forth in Green et al., 32 *Cell* 681 (March 1981). The $^{32}$P-RNA probe was synthesized from a 434 base pair Rsa I to Dra I (nucleotide Nos. 22-506) fragment of the bIL-2 cDNA in FIG. 2, which was subcloned into the pGEM-1 vector (Promega Biotec, Madison, WI). The RNA bound to the nylon membrane was hybridized with the labeled RNA probe ($10^6$ cpm/ml) for 16 hours at 63° C. in Stark's complete buffer: 5×SSC; 50 mM KH$_2$PO$_4$ [pH 2.5]; 1150 μg/ml denatured salmon sperm DNA; 2×Denhardt's solution [0.04% (wt/vol) Ficoll, 0.04% (wt/vol) polyvinyl pyrrolidone, 0.04% (wt/vol) BSA]; 0.1% SDS; 20 mM Na$_2$ EDTA: and, 50% (wt/vol) formamide. After hybridization, the filter was washed at 63° in 6×SSC for two hours and in 0.1×SSC for two hours and then autoradiographed for four hours with intensifying screens at −70°. The results of autoradiography indicated a strongly hybridizing band composed of approximately 1,100 nucleotides in the total RNA from the lymph node cells stimulated with Con A but not in the unstimulated lymph node cells. The results of the Northern blots analysis are consistent with the levels of biological activity measured above for rbIL-2 derived from peripheral blood leukocytes, discussed above.

EXAMPLE 10

Analysis of Bovine Genomic Sequences

To determine the number of IL-2-related genes in bovine genomic DNA, a labeled bIL-2 cDNA probe was hybridized to Southern blots of genomic DNA isolated from bovine peripheral blood leukocytes by standard tehniques such as detailed by Maniatis et al., supra. Ten of the genomic DNA was digested with restricted enzymes expected to cut relatively infrequently. The probe included 506 bp fragment of the bovine cDNA in FIG. 2, from nucleotide numbers 1 to 506. This probe was radiolabeled by nick translation by standard procedures such as set forth in Maniatis et al., supra at 108 and discussed above. Prior to hybridization, 10 μg of bovine genomic DNA was digested to completion with BamH I, EcoR I, or Hind III using standard techniques. The digested bovine DNA was fractionated by electrophoresis in a 0.7% agarose gel with markers of appropriate size. The agarose gel was blotted onto nitrocellulose filters using the method described by Southern, supra. After the transfer process the filter was air-dried and baked for two hours at 80° C. to bind the DNA fragments to the nitrocellulose. Thereafter, the bound DNA was hybridized with the 32P-labeled cDNA probe as set forth in Example 4, supra, then washed extensively with 2×SSC, 0.5% SDS at room temperature followed by washing in 0.1×SSC, 0.5% SDS for 45 minutes at 65° C. After air-drying, the filter was subject to autoradiography at −70° C. which showed that the bovine genomic DNA digested with BamH I, EcoR I, and Hind III resulted in a single band. On this basis, it appears that IL-2 exists as a single-copy gene in bovine genomic DNA.

As will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the examples contained in the foregoing description.

The embodiments of the invention in which an exclusive property or privilege is claimed are defined as follows:

1. A purified and isolated DNA sequence encoding the amino acid sequence of mature bovine interleukin 2 (IL-2).

2. A purified and isolated DNA sequence according to claim 1, consisting essentially of a bIL-2 cDNA corresponding to the nucleic acid sequence of nucleotides 78 to 428 of FIG. 2.

3. A recombinant expression vector comprising a DNA sequence according to claim 1.

4. A recombinant expression vector comprising a DNA sequence according to claim 2.

5. A yeast or bacterial host transformed with a recombinant expression vector according to claim 3.

6. A yeast or bacterial host transformed with a recombinant expression vector according to claim 4.

* * * * *

UNITED STATES PATENT AND TRADEMARK OFFICE
CERTIFICATE OF CORRECTION

PATENT NO. : 4,882,282

DATED : November 21, 1989

INVENTOR(S) : Dirk M. Anderson et al.

It is certified that error appears in the above-identified patent and that said Letters Patent is hereby corrected as shown below:

In claim 1: "428" should read --482--.

Signed and Sealed this

Sixteenth Day of April, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,882,282

DATED : November 21, 1989

INVENTOR(S) : Dirk M. Anderson et al.

It is certified that error appears in the above-identified patent and that said Letters Patent is hereby corrected as shown below:

Col. 22, line 57, "53202" should read --53203--.

Signed and Sealed this

Eighth Day of September, 1992

Attest:

DOUGLAS B. COMER

*Attesting Officer*  *Acting Commissioner of Patents and Trademarks*